US010214752B2

(12) United States Patent
Mordaka

(10) Patent No.: US 10,214,752 B2
(45) Date of Patent: Feb. 26, 2019

(54) BIOSYNTHESIS OF 1,3-BUTANEDIOL

(71) Applicant: INVISTA North America S.á.r.l., Wilmington, DE (US)

(72) Inventor: Pawel Mordaka, Stockton-on-Tees (GB)

(73) Assignee: INVISTA NORTH AMERICA S.A.R.L., Wilmington, DE (US)

(*) Notice: Subject to any disclaimer, the term of this patent is extended or adjusted under 35 U.S.C. 154(b) by 312 days.

(21) Appl. No.: 14/941,405

(22) Filed: Nov. 13, 2015

(65) Prior Publication Data

US 2016/0138052 A1 May 19, 2016

Related U.S. Application Data

(60) Provisional application No. 62/079,954, filed on Nov. 14, 2014.

(51) Int. Cl.

| C12P 7/18 | (2006.01) |
|---|---|
| C12N 9/04 | (2006.01) |
| C12N 9/10 | (2006.01) |
| C12N 9/88 | (2006.01) |
| C12P 7/16 | (2006.01) |
| C12P 7/42 | (2006.01) |
| C07C 31/20 | (2006.01) |
| C12N 9/16 | (2006.01) |
| C12P 19/30 | (2006.01) |

(52) U.S. Cl.
CPC .............. *C12P 7/18* (2013.01); *C07C 31/207* (2013.01); *C12N 9/0006* (2013.01); *C12N 9/1029* (2013.01); *C12N 9/13* (2013.01); *C12N 9/16* (2013.01); *C12N 9/88* (2013.01); *C12P 7/16* (2013.01); *C12P 7/42* (2013.01); *C12P 19/30* (2013.01); *C12Y 101/0108* (2013.01); *C12Y 203/01016* (2013.01); *C12Y 203/01174* (2013.01); *C12Y 208/03* (2013.01); *C12Y 301/02* (2013.01); *C12Y 401/01004* (2013.01); *Y02E 50/10* (2013.01)

(58) Field of Classification Search
CPC .................................... C12N 15/70; C12P 7/18
See application file for complete search history.

(56) References Cited

U.S. PATENT DOCUMENTS

2013/0109064 A1* 5/2013 Osterhout ............. C12P 7/18
435/135

FOREIGN PATENT DOCUMENTS

WO 2012/021478 2/2012

OTHER PUBLICATIONS

Alber et al. "3-Hydroxypropionyl-Coenzyme A Synthetase from Metallosphaera sedula, an Enzyme Involved in Autotrophic CO2 Fixation" (2007) Journal of Bacteriology 190, 1383-1389.

Lindenkamp et al. "A propionate CoA-transferase of Ralstonia eutropha H16 with broad substrate specificity catalyzing the CoA thioester formation of various carboxylic acids" (2012) Applied Microbiology and Microtechnology 17, 7699-7709.
Valentin et al. "Application of enzymatically synthesized short-chain-length hydroxy fatty acid coenzyme A thioesters for assay of polyhydroxyalkanoic acid synthases" Applied Microbiology and Biotechnology 40, 699-709.
International Search Report and Written Opinion in PCT/US2015/060664 dated Apr. 13, 2016.
International Preliminary Report on Patentability in PCT/US2015/060664 dated May 26, 2017.
Becker et al., "Metabolic Flux Engineering of I-lysine Production in Corynebacterium Glutamicum—Over Expression and Modification of G6P Dehydrogenase", Journal of Biotechnology, vol. 132, Issue 2, Oct. 31, 2007, pp. 99-109.
Brigham et al., "Engineering Ralstonia eutropha for Production of Isobutanol from CO2, H2, and O2", Advanced Biofuels and Bioproducts, Chapter 39, Jan. 2013, pp. 1065-1090.
Bugg et al., "The Emerging Role for Bacteria in Lignin Degradation and Bio-product Formation", Current Opinion in Biotechnology, vol. 22, Issue 3, Jun. 2011, pp. 394-400.
Cantu et al., "Thioesterases: A New Perspective Based on Their Primary and Tertiary Structures", Protein Science, vol. 19, Issue 7, May 17, 2010, pp. 1281-1295.
Zhuang et al., "Divergence of Function in the Hot Dog Fold Enzyme Superfamily: The Bacterial Thioesterase YciA†", Biochemistry, vol. 47, No. 9, Feb. 2, 2008, pp. 2789-2796.
Haywood et al., "Characterization of Two 3-Ketothiolases Possessing Differing Substrate Specificities in the Polyhydroxyalkanoate Synthesizing Organism Alcaligenes Eutrophus", FEMS Microbiology Letters, vol. 52, Issues 1-2, Jul. 1988, pp. 91-96.
Hermann, Thomas, "Industrial Production of Amino Acids by Coryneform Bacteria", Journal of Biotechnology, vol. 104, Issues 1-3, Sep. 4, 2003, pp. 155-172.
Jaremko et al., "The Initial Metabolic Conversion of Levulinic Acid in Cupriavidus Necator", Journal of Biotechnology, vol. 155, Issue 3, Sep. 20, 2011, pp. 293-298.
Köpke et al., "2,3-Butanediol Production by Acetogenic Bacteria, an Alternative Route to Chemical Synthesis, Using Industrial Waste Gas", Applied and Environmental Microbiology, vol. 77, No. 15, Aug. 2011, pp. 5467-5475.
Lee et al., "Synthesis of Pure meso-2,3-Butanediol from Crude Glycerol Using an Engineered Metabolic Pathway in *Escherichia coli*", Applied Biochemistry and Biotechnology, vol. 166, Issue 7, Apr. 2012, pp. 1801-1813.
Lee et al., "Metabolic Engineering of Pentose Phosphate Pathway in Ralstoniaeutropha for Enhanced Biosynthesis of Poly-β-Hydroxybutyrate", Biotechnology Progress, vol. 19, Issue 5, 2003, pp. 1444-1449.

(Continued)

*Primary Examiner* — Maryam Monshipouri
(74) *Attorney, Agent, or Firm* — Licata & Tyrrell P.C.; William J. Simmons

(57) ABSTRACT

This document describes biochemical pathways for producing 1,3-butanediol using a polypetide having β-ketothiolase activity to form a 3-oxo-5-hydroxypentanoyl-CoA intermediate that can be enzymatically converted to 1,3-butanediol, as well as recombinant hosts producing 1,3-butanediol.

2 Claims, 5 Drawing Sheets
Specification includes a Sequence Listing.

(56) References Cited

OTHER PUBLICATIONS

Li et al., "Cupriavidus necator JMP134 rapidly reduces furfural with a Zn-dependent alcohol dehydrogenas", Biodegradation, 22, Apr. 28, 2011, pp. 1215-1225.

Lim et al., "Amplification of the NADPH-Related Genes zwf and gnd for the Oddball Biosynthesis of PHB in an *E. coli* Transformant Harboring a Cloned phbCAB Operon", Journal of Bioscience and Bioengineering, vol. 93, Issue 6, 2002, pp. 543-549.

Martin et al., "A Platform Pathway for Production of 3-Hydroxyacids Provides a Biosynthetic Route to 3-Hydroxy-γ-Butyrolactone", Nature Communications 4, Article No. 1414, Jan. 29, 2013, 10 pages.

Martin et al., "High-titer Production of Monomeric Hydroxyvalerates From Levulinic Acid in Pseudomonas Putida", Journal of Biotechnology, vol. 139, Issue 1, Jan. 1, 2009, pp. 61-67.

Meijnen et al., "Improved p-hydroxyBenzoate Production by Engineered Pseudomonas Putida S12 by Using a Mixed-substrate Feeding Strategy", Applied Microbiology and Biotechnology, vol. 90, Feb. 2, 2011, pp. 885-893.

Naggert et al., "Cloning, Sequencing, and Characterization of *Escherichia coli* Thioesterase 11", Journal of Biological Chemistry, vol. 266, No. 17, 1991, pp. 11044-11050.

Nogales et al., "Characterization of the Last Step of the Aerobic Phenylacetic Acid Degradation Pathway", Microbiology, vol. 153, Feb. 2007, pp. 357-365.

Ohashi et al., "Continuous Production of Lactic Acid from Molasses by Perfusion Culture of Lactococcus Lactis Using a Stirred Ceramic Membrane Reactor", Journal of Bioscience and Bioengineering, vol. 87, Issue 5, 1999, pp. 647-654.

Papanikolaou et al., "Citric Acid Production by Yarrowia Lipolytica Cultivated on Olive-Mill Wastewater-Based Media", Bioresource Technology, vol. 99, Issue 7, 2008, pp. 2419-2428.

Perez-Pantoja et al., "Metabolic Reconstruction of Aromatic Compounds Degradation from the Genome of the Amazing Pollutant-Degrading Bacterium Cupriavidus Necator JMP134", FEMS Microbialogy Reviews, vol. 32, 2008, pp. 736-794.

Prybylski et al., "Third-Generation Feed Stocks for the Clean and Sustainable Biotechnological Production of Bulk Chemicals: Synthesis of 2-Hydroxyisobutyric Acid", Energy, Sustainability and Society, vol. 2, No. 11, Jul. 16, 2012, 9 pages.

Ramsay et al., "Use of a Nylon Manufacturing Waste as an Industrial Fermentation Substrate", Applied and Environmental Microbiology, vol. 52, No. 1, Jul. 1986, pp. 152-156.

Satoh et al., "Enzyme-catalyzed poly(3-hydroxybutyrate) synthesis from acetate with CoA recycling and NADPH regeneration in Vitro", Journal of Bioscience and Bioengineering, vol. 95, Issue 4, 2003, pp. 335-341.

Seedorf et al., "The Genome of Clostridium Kluyveri, A Strict Anaerobe with Unique Metabolic Features", PNAS USA, vol. 105, No. 6, Feb. 12, 2008, pp. 2128-2133.

Shen et al., "Driving Forces Enable High-Titer Anaerobic 1-Butanol Synthesis in *Escherichia coli*", Applied and Environmental Microbiology, vol. 77, No. 9, May 2011, pp. 2905-2915.

Slater et al., "Multiple β-Ketothiolases Mediate Poly(β-Hydroxyalkanoate) Copolymer Synthesis in Ralstonia eutropha", Journal of Bacteriology, vol. 180 No. 8, Apr. 1998, pp. 1979-1987.

Stanbury et al., "Principles of Fermentation Technology", 2nd edition, 1995, 367 pages (Table of Contents Attached).

Wee et al., "Biotechnological Production of Lactic Acid and Its Recent Applications", Food Technology and Biotechnology, vol. 44, No. 2, 2006, pp. 163-172.

Yang et al., "Value-added Uses for Crude Glycerol—a Byproduct of Biodiesel Production", Biotechnology for Biofuels, vol. 5, No. 13, Mar. 14, 2012, 10 pages.

Zhang et al., "Enhancing Fatty Acid Production by the Expression of the Regulatory Transcription Factor FadR", Metabolic Engineering, vol. 14, Sep. 28, 2012, pp. 653-660.

\* cited by examiner

FIGURE 2

| SEQ ID NO | Organism | GENBANK reference | Amino acid sequence |
|---|---|---|---|
| 1 | Cupriavidus necator | AAC38322.1 | MTREVVVSGVRTAIGTFGGSLKDVAPAELGALVVREALARAQVSGDDVGHVVFGNVIQT EPRDMYLGRVAAVNGGVTINAPALTVNRLCGSGLQAIVSAAQTILLGDTDVAIGGGAESM SRAPYLAPAARWGARMGDAGLVDMMLGALHDPFHRIHMGVTAENVAKEYDISRAQQDEAA LESHRRASAAIKAGYFKDQIVPVVSKGRKGDVTFDTDEHVRHDATIDDMTKLRPVFVKEN GTVTAGNASGLNDAAAAVVMMERAEAERRGLKPLARLVSYGHAGVDPKAMGIGPVPATKI ALERAGLQVSDLDVIEANEAFAAQACAVTKALGLDPAKVNPNGSGISLGHPIGATGALIT VKALHELNRVQGRYALVTMCIGGGQGIAAIFERI |
| 2 | Escherichia coli | AAC74479.1 | MREAFICDGIRTPIGRYGGALSSVRADDLAAIPLRELLVRNPRLDAECIDDVILGCANQA GEDNRNVARMATLLAGLPQSVSGTTINRLCGSGLDALGFAARAIKAGDGDLLIAGGVESM SRAPFVMGKAASAFSRQAEMFDTTIGWRFVNPLMAQQFGTDSMPETAENVAELLKISRED QDSFALRSQQRTAKAQSSGILAEEIVPVVLKNKGVVTEIQHDEHLRPETTLEQLRGLKA PFRANGVITAGNASGVNDGAAALIIASEQMAAAAQGLTPRARIVAMATAGVEPRLMGLGPV PATRRVLERAGLSIHDMDVIELNEAFAAQALGVLRELGLPDDAPHVNPNGGAIALGHPLG MSGARLALAASHELHRRNGRYALCTMCIGVGQGIAMILERV |
| 3 | Escherichia coli | AAA24665.1 | MSQALKNLLTLLNLEKIEEGLFRGQSEDLGLRQVFGGQVVGQALYAAKETVPEERLVHSF HSYFLRPGDSKKPIIYDVETLRDGNSFSARRVAAIQNGKPIFYMTASFQAPEAGFEHQKT MPSAPAPDGLPSETQIAQSLAHLLPPVLKDKFICDRPLEVRPVEFHNPLKGHVAEPHRQV WIRANGSVPDDLRVHQYLLGYASDLNFLPVALQPHGIGFLEPGIQIATIDHSMWFHRPFN LNEWLLYSVESTSASSARGFVRGEFYTQDGVLVASTVQEGVMRNHN |
| 4 | Micrococcus luteus | ADD83022.1 | MSEFTRFEQVTVLGTGVLGSQIIMQAAYHGKKVMAYDAVPAALENLDKRWAWIRQGYEAD LGEGYDAARFDEAIARITPTSDLAEAVADADIVIEAVPENLELKRKVWAQVGELAPATTL FATNTSSLLPSDFFADASGHPERFLALHYANRIWAQNTAEVMGTAATSPEAVAGALQFAEE TGMVPVHVRKEIPGYFLNSLLIPWLQAGSKLYMHGVGNPADIDRTWRVATGNERGPFQTY DIVGFHVAANVSRNTGVDWQLGFAEMLEKSIAEGHSGVADGQGFYRYGPDGENLGPVEDW NLGDKDTPLG |

FIGURE 2 (Continued)

| SEQ ID NO | Organism | GENBANK reference | Amino acid sequence |
|---|---|---|---|
| 5 | Escherichia coli | AAC75282.1 | MDAKQRIARRVAQELRDGDIVNLGIGLPTMVANYLPEGIHTLQSENGFLGLGPVTTAHP DLVNAGGQPCGVLPGAAMFDSAMSFALIRGGHIDACVLGGLQVDEEANLANWVVPGKMVP GMGGAMDLVTGSRKVIIAMEHCAKDGSAKILRRCTMPLTAQHAVHMLVTELAVFRFIDGK MWLTEIADGCDLATVRAKTEARFEVAADLNTQRGDL |
|  |  | AAC75281.1 | MKTKLMTLQDATGFFRDGMTIMVGGFMGIGTPSRLVEALLESGVRDLTLIANDTAFVDTG IGPLIVNGRVRKVIASHIGTNPETGRRMISGEMDVVLVPQGTLIEQIRCGGAGLGGFLTP TGVGTVVEEGKQTLTLDGKTWLLERPLRADLALIRAHRCDTLGNLTYQLSARNFNPLIAL AADITLVEPDELVETGELQPDHIVTPGAVIDHIIVSQESK |
| 6 | Pseudomonas putida | ACA73091.1 | MINKTYESIASAVEGITDGSTIMVGGFGTAGMPSELIDALIDTGTRDLTIISNNAGNGEI GLAALLKAGSVRKVVCSFPRQSDSYVFDELYRAGKIELEVVPQGNLAERIRAAGSGIGAF FSPTGYGTLLSEGKETREIDGRQYVLEMPLHADFALIKAYKGDRWGNLIYRKAARNFGPI MAMAAKTAIAQVDQIVELGELDPEHIITPGIFVQRVVAVTGAASSIA |
|  |  | ACA73090.1 | MTITTKLSRTQMAQRVAADIQEGAYVNLGIGAPTLVANFLGDKEVFLHSENGLLGMGPSP APGEEDDLINAGKQHVTLLTGGAFFHHADSFSMMRGGHLDIAVLGAFQVSVKGDLANWH TGAEGSIPAVGGAMDLATGARQVFVMMDHLTKSGESKIVPECTYPLTGIGCVSRIYTDLA VLEVTSDGLKVVEICADIDFDELQKLSGVPLIK |
| 7 | Clostridium propionicum | CAB77207.1 | MRKVPIITADEAAKLIKDGDTVTTSGFVGNAIPEALDRAVEKRFLETGEPKNITYVYCGS QGNRDGRGAEHFAHEGLLKRYIAGHWATVPALGKMAMENKMEAYNVSQGALCHLFRDIAS HKPGVFTKVGIGTFIDPRNGGGKVNDITKEDIVELVEIKGQEYLFYPAFPIHVALIRGTY ADESGNITFEKEVAPLEGTSVCQAVKNSGGIVVVQVERVVKAGTLDPRHVKVPGIYVDYV VVADPEDHQQSLDCEYDPALSGEHRRPEVVGEPLPLSAKKVIGRRGAIELEKDVAVNLGV GAPEYVASVADEEGIVDFMTLTAESGAIGGVPAGGVRFGASYNADALIDQGYQFDYYDGG GLDLCYLGLAECDEKGNINVSRFGPRIAGCGGFINITQNTPKVFFCGTFTAGGLKVKIED GKVIIVQEGKQKFLKAVEQITFNGDVALANKQQVTYITERCVFLLKEDGLHLSEIAPGI DLQTQILDVMDFAPIIDRDANGQIKLMDAALFAEGLMGLKEMKS |

FIGURE 2 (Continued)

| SEQ ID NO | Organism | GENBANK reference | Amino acid sequence |
|---|---|---|---|
| 8 | Chromobacterium violaceum | AAQ61181.1 | MKQQEVRQRAFAMPLTSPAFFPGPYRFVNREYMIITYRTDPAAIEAVLPEPLQMAEPVVR YEFIRMPDSTGFGDYSESGQVIPVTFRGERGSYTLAMFLDDQPPLAGGRELWGPKKAGK PRLEVHQDTLVGSLDFGPVRIATGTMGYKYEALDRSALLASLAEPNFLLKIIPHVDGSPR ICELVRYHTTDVAIKGAWSAPGSLELHPHALAPVAALPVLEVLSARHFVCDLTLDLGTVV FDYLRQ |
| 9 | Lactobacillus brevis | CAD66648.1 | MSNRLDGKVAIITGGTLGIGLAIATKFVEEGAKVMITGRHSDVGEKAAKSVGTPDQIQFFQHDSSDEDGWTKLFDATEKAF GPVSTLVNNAGIAVNKSVEETTTAEWRKLLAVNLDGVFFGTRLGIQRMKNKGLGASIINMSSIEGFVGDPSLGAYNASKG AVRIMSKSAALDCALKDYDVRVNTVHPGYIKTPLVDDLPGAEEAMSQRTKTPMGHIGEPNDIAYICVYLASNESKFATGS EFVVDGGYTAQ |
| 10 | Clostridium acetobutylicum | AAA63761.1 | MLKDEVIKQISTPLTSPAFPRGPYKFHNREYFNIVYRTDMDALRKVVPEPLEIDEPLVRF EIMAMHDTSGLGCYTESGQAIPVSFNGVKGDYLHMMYLDNEPAIAVGRELSAYPKKLGYP KLFVDSDTLVGTLDYGKLRVATATMGYKHKALDANEAKDQICRPNYMLKIIPNYDGSPRI CELINAKITDVTVHEAWTGPTRLQLFDHAMAPLNDLPVKEIVSSSHILADIILPRAEVIY DYLK |
| 11 | Clostridium beijerinckii | AAA23199.2 | MKGFAMLGINKLGWIEKERPVAGSYDAIVRPLAVSPCTSDIHTVFEGALGDRKNMILGHE AVGEVVEVGSEVKDFKPGDRVIVPCTTPDWRSLEVQAGFQQHSNGMLAGWKFSNFKDGVF GEYFHVNDADMNLAILPKDMPLENAVMITDMMTTGFHGAELADIQMGSSVVVIGIGAVGL MGIAGAKLRGAGRIIGVGSRPICVEAAKFYGATDILNYKNGHIVDQVMKLTNGKGVDRVI MAGGSETLSQAVSMVKPGGIISNINYHGSGDALLIPRVEWGCGMAHKTIKGGLCPGGRL RAEMLRDMVVYNRVDLSKLVTHVYHGFDHIEEALLLMKDKPKDLIKAVVIL |
| 12 | Cupriavidus necator | CAJ93797.1 | MKVITAREAAALVQDGWTVASAGFVGAGHAEAVTEALEQRFLQSGLPRDLTLVYSAGQGD RGARGVNHFGNAGMTASIVGGHWRSATRLATILAMAEQCEGYNLPQGVLTHLYRAIAGGKP GVMTKIGLHTFVDPRTAQDARYHGGAVNERARQAIAEGKACWVDAVDFRGDEYLFYPSFP IHCALIRCTAADARGNLSTHREAFHHELLAMAQAAHNSGGIVIAQVESLVDHHEILQAIH VPGILVDYVVVCDNPANHQMTFAESYNPAYVTPWQGEAAVAEAEAAPVAAGPLDARTIVQ RRAVMELARRAPRVVNLGVGMPAAVGMLAHQAGLDGFTLTVEAGPIGGTPADGLSFGASA YPEAVVDQPAQFDFYEGGGIDLAILGLAELDGHGNVNVSKFGEGEGASIAGVGGFINITQ SARAVVFMGTLTAGGLEVRAGDGGLQIVREGRVKKIVPEVSHLSFNGPYVASLGIPVLYI TERAVFEMRAGADGEARLTLVEIAPGVDLQRDVLDQCSTPIAVAQDLREMDARLFQAGPL HL |

FIGURE 2 (Continued)

| SEQ ID NO | Organism | GENBANK reference | Amino acid sequence |
|---|---|---|---|
| 13 | Clostridium aminobutyricum | CAB60036.2 | MDWKKIYEDRTCTADEAVKSIKSGDRVLFAHCVAEPPVLVEAMVANAAAYKNVTVSHMVTLGKGEYSKPEYKENFTFEGWFTSPSTRGSIAEGHGQFVPVFFHEVPSLIRKDIFHVDVFMVMVSPPDHNGFCCVGVSSDYTMQAIKSAKIVLAEVNDQVPVVYGDTFVHVSEIDKFVETSHPLPEIGLPKIGEVEAAIGKHCASLIEDGSTLQLGIGAIPDAVLSQLKDKKHLGIHSEMISDGVVDLYEAGVIDCSQKSIDKGKMAITFLMGTKRLYDFAANNPKVELKPVDYINHPSVVAQCSKMVCINACLQVDFMGQIVSDSIGTKQFSGVGGQVDFVRGASMSIDGKGKAIIAMPSVAKKDGSMISKIVPFIDHGAAVTTSRNDADYVVTEYGIAEMKGKSLQDRARALINIAHPDFKDELKAEFEKRFNAAF |
| 14 | Escherichia coli | AAB60068.1 | MSTTHNVPQGDLVLRTLAMPADTNANGDIFGGWLMSQMDIGGAILAKEIAHGRVVTVRVEGMTFLRPVAVGDVVCCYARCVQKGTTSVSINIEVWVKKVASEPIGQRYKATEALFKYVAVDPEGKPRALPVE | ns

SEQUENCE LISTING

```
<160> NUMBER OF SEQ ID NOS: 14

<210> SEQ ID NO 1
<211> LENGTH: 394
<212> TYPE: PRT
<213> ORGANISM: Cupriavidus necator

<400> SEQUENCE: 1

Met Thr Arg Glu Val Val Val Ser Gly Val Arg Thr Ala Ile Gly
 1               5                  10                  15

Thr Phe Gly Gly Ser Leu Lys Asp Val Ala Pro Ala Glu Leu Gly Ala
                20                  25                  30

Leu Val Val Arg Glu Ala Leu Ala Arg Ala Gln Val Ser Gly Asp Asp
                35                  40                  45

Val Gly His Val Val Phe Gly Asn Val Ile Gln Thr Glu Pro Arg Asp
    50                  55                  60

Met Tyr Leu Gly Arg Val Ala Ala Val Asn Gly Gly Val Thr Ile Asn
65                  70                  75                  80

Ala Pro Ala Leu Thr Val Asn Arg Leu Cys Gly Ser Gly Leu Gln Ala
                85                  90                  95

Ile Val Ser Ala Ala Gln Thr Ile Leu Leu Gly Asp Thr Asp Val Ala
                100                 105                 110

Ile Gly Gly Gly Ala Glu Ser Met Ser Arg Ala Pro Tyr Leu Ala Pro
            115                 120                 125

Ala Ala Arg Trp Gly Ala Arg Met Gly Asp Ala Gly Leu Val Asp Met
        130                 135                 140

Met Leu Gly Ala Leu His Asp Pro Phe His Arg Ile His Met Gly Val
145                 150                 155                 160

Thr Ala Glu Asn Val Ala Lys Glu Tyr Asp Ile Ser Arg Ala Gln Gln
                165                 170                 175

Asp Glu Ala Ala Leu Glu Ser His Arg Arg Ala Ser Ala Ala Ile Lys
            180                 185                 190

Ala Gly Tyr Phe Lys Asp Gln Ile Val Pro Val Val Ser Lys Gly Arg
        195                 200                 205

Lys Gly Asp Val Thr Phe Asp Thr Asp Glu His Val Arg His Asp Ala
    210                 215                 220
```

```
Thr Ile Asp Asp Met Thr Lys Leu Arg Pro Val Phe Val Lys Glu Asn
225                 230                 235                 240

Gly Thr Val Thr Ala Gly Asn Ala Ser Gly Leu Asn Asp Ala Ala Ala
            245                 250                 255

Ala Val Val Met Met Glu Arg Ala Glu Ala Glu Arg Arg Gly Leu Lys
        260                 265                 270

Pro Leu Ala Arg Leu Val Ser Tyr Gly His Ala Gly Val Asp Pro Lys
            275                 280                 285

Ala Met Gly Ile Gly Pro Val Pro Ala Thr Lys Ile Ala Leu Glu Arg
        290                 295                 300

Ala Gly Leu Gln Val Ser Asp Leu Asp Val Ile Glu Ala Asn Glu Ala
305                 310                 315                 320

Phe Ala Ala Gln Ala Cys Ala Val Thr Lys Ala Leu Gly Leu Asp Pro
                325                 330                 335

Ala Lys Val Asn Pro Asn Gly Ser Gly Ile Ser Leu Gly His Pro Ile
            340                 345                 350

Gly Ala Thr Gly Ala Leu Ile Thr Val Lys Ala Leu His Glu Leu Asn
        355                 360                 365

Arg Val Gln Gly Arg Tyr Ala Leu Val Thr Met Cys Ile Gly Gly Gly
    370                 375                 380

Gln Gly Ile Ala Ala Ile Phe Glu Arg Ile
385                 390

<210> SEQ ID NO 2
<211> LENGTH: 401
<212> TYPE: PRT
<213> ORGANISM: Escherichia coli

<400> SEQUENCE: 2

Met Arg Glu Ala Phe Ile Cys Asp Gly Ile Arg Thr Pro Ile Gly Arg
  1               5                  10                  15

Tyr Gly Gly Ala Leu Ser Ser Val Arg Ala Asp Asp Leu Ala Ala Ile
             20                  25                  30

Pro Leu Arg Glu Leu Leu Val Arg Asn Pro Arg Leu Asp Ala Glu Cys
         35                  40                  45

Ile Asp Asp Val Ile Leu Gly Cys Ala Asn Gln Ala Gly Glu Asp Asn
 50                  55                  60

Arg Asn Val Ala Arg Met Ala Thr Leu Leu Ala Gly Leu Pro Gln Ser
 65                  70                  75                  80

Val Ser Gly Thr Thr Ile Asn Arg Leu Cys Gly Ser Gly Leu Asp Ala
             85                  90                  95

Leu Gly Phe Ala Ala Arg Ala Ile Lys Ala Gly Asp Gly Asp Leu Leu
            100                 105                 110

Ile Ala Gly Gly Val Glu Ser Met Ser Arg Ala Pro Phe Val Met Gly
        115                 120                 125

Lys Ala Ala Ser Ala Phe Ser Arg Gln Ala Glu Met Phe Asp Thr Thr
        130                 135                 140

Ile Gly Trp Arg Phe Val Asn Pro Leu Met Ala Gln Gln Phe Gly Thr
145                 150                 155                 160

Asp Ser Met Pro Glu Thr Ala Glu Asn Val Ala Glu Leu Leu Lys Ile
                165                 170                 175

Ser Arg Glu Asp Gln Asp Ser Phe Ala Leu Arg Ser Gln Gln Arg Thr
            180                 185                 190

Ala Lys Ala Gln Ser Ser Gly Ile Leu Ala Glu Glu Ile Val Pro Val
        195                 200                 205
```

```
Val Leu Lys Asn Lys Lys Gly Val Val Thr Glu Ile Gln His Asp Glu
    210                 215                 220

His Leu Arg Pro Glu Thr Thr Leu Glu Gln Leu Arg Gly Leu Lys Ala
225                 230                 235                 240

Pro Phe Arg Ala Asn Gly Val Ile Thr Ala Gly Asn Ala Ser Gly Val
                245                 250                 255

Asn Asp Gly Ala Ala Ala Leu Ile Ile Ala Ser Glu Gln Met Ala Ala
                260                 265                 270

Ala Gln Gly Leu Thr Pro Arg Ala Arg Ile Val Ala Met Ala Thr Ala
            275                 280                 285

Gly Val Glu Pro Arg Leu Met Gly Leu Gly Pro Val Pro Ala Thr Arg
290                 295                 300

Arg Val Leu Glu Arg Ala Gly Leu Ser Ile His Asp Met Asp Val Ile
305                 310                 315                 320

Glu Leu Asn Glu Ala Phe Ala Ala Gln Ala Leu Gly Val Leu Arg Glu
                325                 330                 335

Leu Gly Leu Pro Asp Asp Ala Pro His Val Asn Pro Asn Gly Gly Ala
                340                 345                 350

Ile Ala Leu Gly His Pro Leu Gly Met Ser Gly Ala Arg Leu Ala Leu
            355                 360                 365

Ala Ala Ser His Glu Leu His Arg Arg Asn Gly Arg Tyr Ala Leu Cys
        370                 375                 380

Thr Met Cys Ile Gly Val Gly Gln Gly Ile Ala Met Ile Leu Glu Arg
385                 390                 395                 400

Val

<210> SEQ ID NO 3
<211> LENGTH: 286
<212> TYPE: PRT
<213> ORGANISM: Escherichia coli

<400> SEQUENCE: 3

Met Ser Gln Ala Leu Lys Asn Leu Leu Thr Leu Leu Asn Leu Glu Lys
1               5                   10                  15

Ile Glu Glu Gly Leu Phe Arg Gly Gln Ser Glu Asp Leu Gly Leu Arg
            20                  25                  30

Gln Val Phe Gly Gly Gln Val Val Gly Gln Ala Leu Tyr Ala Ala Lys
        35                  40                  45

Glu Thr Val Pro Glu Glu Arg Leu Val His Ser Phe His Ser Tyr Phe
50                  55                  60

Leu Arg Pro Gly Asp Ser Lys Lys Pro Ile Ile Tyr Asp Val Glu Thr
65                  70                  75                  80

Leu Arg Asp Gly Asn Ser Phe Ser Ala Arg Arg Val Ala Ala Ile Gln
                85                  90                  95

Asn Gly Lys Pro Ile Phe Tyr Met Thr Ala Ser Phe Gln Ala Pro Glu
            100                 105                 110

Ala Gly Phe Glu His Gln Lys Thr Met Pro Ser Ala Pro Ala Pro Asp
        115                 120                 125

Gly Leu Pro Ser Glu Thr Gln Ile Ala Gln Ser Leu Ala His Leu Leu
    130                 135                 140

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
                165                 170                 175
```

His Arg Gln Val Trp Ile Arg Ala Asn Gly Ser Val Pro Asp Asp Leu
                180                 185                 190

Arg Val His Gln Tyr Leu Leu Gly Tyr Ala Ser Asp Leu Asn Phe Leu
            195                 200                 205

Pro Val Ala Leu Gln Pro His Gly Ile Gly Phe Leu Glu Pro Gly Ile
        210                 215                 220

Gln Ile Ala Thr Ile Asp His Ser Met Trp Phe His Arg Pro Phe Asn
225                 230                 235                 240

Leu Asn Glu Trp Leu Leu Tyr Ser Val Glu Ser Thr Ser Ala Ser Ser
                245                 250                 255

Ala Arg Gly Phe Val Arg Gly Glu Phe Tyr Thr Gln Asp Gly Val Leu
            260                 265                 270

Val Ala Ser Thr Val Gln Glu Gly Val Met Arg Asn His Asn
        275                 280                 285

<210> SEQ ID NO 4
<211> LENGTH: 310
<212> TYPE: PRT
<213> ORGANISM: Micrococcus luteus

<400> SEQUENCE: 4

Met Ser Glu Phe Thr Arg Phe Glu Gln Val Thr Val Leu Gly Thr Gly
1               5                   10                  15

Val Leu Gly Ser Gln Ile Ile Met Gln Ala Ala Tyr His Gly Lys Lys
                20                  25                  30

Val Met Ala Tyr Asp Ala Val Pro Ala Ala Leu Glu Asn Leu Asp Lys
            35                  40                  45

Arg Trp Ala Trp Ile Arg Gln Gly Tyr Glu Ala Asp Leu Gly Glu Gly
    50                  55                  60

Tyr Asp Ala Ala Arg Phe Asp Glu Ala Ile Ala Arg Ile Thr Pro Thr
65                  70                  75                  80

Ser Asp Leu Ala Glu Ala Val Ala Asp Ala Asp Ile Val Ile Glu Ala
                85                  90                  95

Val Pro Glu Asn Leu Glu Leu Lys Arg Lys Val Trp Ala Gln Val Gly
            100                 105                 110

Glu Leu Ala Pro Ala Thr Thr Leu Phe Ala Thr Asn Thr Ser Ser Leu
        115                 120                 125

Leu Pro Ser Asp Phe Ala Asp Ala Ser Gly His Pro Glu Arg Phe Leu
130                 135                 140

Ala Leu His Tyr Ala Asn Arg Ile Trp Ala Gln Asn Thr Ala Glu Val
145                 150                 155                 160

Met Gly Thr Ala Ala Thr Ser Pro Glu Ala Val Ala Gly Ala Leu Gln
                165                 170                 175

Phe Ala Glu Glu Thr Gly Met Val Pro Val His Val Arg Lys Glu Ile
            180                 185                 190

Pro Gly Tyr Phe Leu Asn Ser Leu Leu Ile Pro Trp Leu Gln Ala Gly
        195                 200                 205

Ser Lys Leu Tyr Met His Gly Val Gly Asn Pro Ala Asp Ile Asp Arg
210                 215                 220

Thr Trp Arg Val Ala Thr Gly Asn Glu Arg Gly Pro Phe Gln Thr Tyr
225                 230                 235                 240

Asp Ile Val Gly Phe His Val Ala Ala Asn Val Ser Arg Asn Thr Gly
                245                 250                 255

Val Asp Trp Gln Leu Gly Phe Ala Glu Met Leu Glu Lys Ser Ile Ala
            260                 265                 270

Glu Gly His Ser Gly Val Ala Asp Gly Gln Gly Phe Tyr Arg Tyr Gly
            275                 280                 285

Pro Asp Gly Glu Asn Leu Gly Pro Val Glu Asp Trp Asn Leu Gly Asp
    290                 295                 300

Lys Asp Thr Pro Leu Gly
305                 310

<210> SEQ ID NO 5
<211> LENGTH: 436
<212> TYPE: PRT
<213> ORGANISM: Escherichia coli

<400> SEQUENCE: 5

Met Asp Ala Lys Gln Arg Ile Ala Arg Arg Val Ala Gln Glu Leu Arg
1               5                   10                  15

Asp Gly Asp Ile Val Asn Leu Gly Ile Gly Leu Pro Thr Met Val Ala
            20                  25                  30

Asn Tyr Leu Pro Glu Gly Ile His Ile Thr Leu Gln Ser Glu Asn Gly
        35                  40                  45

Phe Leu Gly Leu Gly Pro Val Thr Thr Ala His Pro Asp Leu Val Asn
    50                  55                  60

Ala Gly Gly Gln Pro Cys Gly Val Leu Pro Gly Ala Ala Met Phe Asp
65                  70                  75                  80

Ser Ala Met Ser Phe Ala Leu Ile Arg Gly Gly His Ile Asp Ala Cys
                85                  90                  95

Val Leu Gly Gly Leu Gln Val Asp Glu Glu Ala Asn Leu Ala Asn Trp
            100                 105                 110

Val Val Pro Gly Lys Met Val Pro Gly Met Gly Gly Ala Met Asp Leu
        115                 120                 125

Val Thr Gly Ser Arg Lys Val Ile Ile Ala Met Glu His Cys Ala Lys
    130                 135                 140

Asp Gly Ser Ala Lys Ile Leu Arg Arg Cys Thr Met Pro Leu Thr Ala
145                 150                 155                 160

Gln His Ala Val His Met Leu Val Thr Glu Leu Ala Val Phe Arg Phe
                165                 170                 175

Ile Asp Gly Lys Met Trp Leu Thr Glu Ile Ala Asp Gly Cys Asp Leu
            180                 185                 190

Ala Thr Val Arg Ala Lys Thr Glu Ala Arg Phe Glu Val Ala Ala Asp
        195                 200                 205

Leu Asn Thr Gln Arg Gly Asp Leu Met Lys Thr Lys Leu Met Thr Leu
    210                 215                 220

Gln Asp Ala Thr Gly Phe Phe Arg Asp Gly Met Thr Ile Met Val Gly
225                 230                 235                 240

Gly Phe Met Gly Ile Gly Thr Pro Ser Arg Leu Val Glu Ala Leu Leu
                245                 250                 255

Glu Ser Gly Val Arg Asp Leu Thr Leu Ile Ala Asn Asp Thr Ala Phe
            260                 265                 270

Val Asp Thr Gly Ile Gly Pro Leu Ile Val Asn Gly Arg Val Arg Lys
        275                 280                 285

Val Ile Ala Ser His Ile Gly Thr Asn Pro Glu Thr Gly Arg Arg Met
    290                 295                 300

Ile Ser Gly Glu Met Asp Val Val Leu Val Pro Gln Gly Thr Leu Ile
305                 310                 315                 320

Glu Gln Ile Arg Cys Gly Gly Ala Gly Leu Gly Gly Phe Leu Thr Pro
                325                 330                 335

```
Thr Gly Val Gly Thr Val Val Glu Glu Gly Lys Gln Thr Leu Thr Leu
            340                 345                 350

Asp Gly Lys Thr Trp Leu Leu Glu Arg Pro Leu Arg Ala Asp Leu Ala
            355                 360                 365

Leu Ile Arg Ala His Arg Cys Asp Thr Leu Gly Asn Leu Thr Tyr Gln
            370                 375                 380

Leu Ser Ala Arg Asn Phe Asn Pro Leu Ile Ala Leu Ala Ala Asp Ile
385                 390                 395                 400

Thr Leu Val Glu Pro Asp Glu Leu Val Glu Thr Gly Glu Leu Gln Pro
                405                 410                 415

Asp His Ile Val Thr Pro Gly Ala Val Ile Asp His Ile Ile Val Ser
            420                 425                 430

Gln Glu Ser Lys
            435

<210> SEQ ID NO 6
<211> LENGTH: 440
<212> TYPE: PRT
<213> ORGANISM: Pseudomonas putida

<400> SEQUENCE: 6

Met Ile Asn Lys Thr Tyr Glu Ser Ile Ala Ser Ala Val Glu Gly Ile
1               5                   10                  15

Thr Asp Gly Ser Thr Ile Met Val Gly Gly Phe Gly Thr Ala Gly Met
            20                  25                  30

Pro Ser Glu Leu Ile Asp Ala Leu Ile Asp Thr Gly Thr Arg Asp Leu
            35                  40                  45

Thr Ile Ile Ser Asn Asn Ala Gly Asn Gly Glu Ile Gly Leu Ala Ala
50                  55                  60

Leu Leu Lys Ala Gly Ser Val Arg Lys Val Val Cys Ser Phe Pro Arg
65                  70                  75                  80

Gln Ser Asp Ser Tyr Val Phe Asp Glu Leu Tyr Arg Ala Gly Lys Ile
            85                  90                  95

Glu Leu Glu Val Val Pro Gln Gly Asn Leu Ala Glu Arg Ile Arg Ala
            100                 105                 110

Ala Gly Ser Gly Ile Gly Ala Phe Phe Ser Pro Thr Gly Tyr Gly Thr
            115                 120                 125

Leu Leu Ser Glu Gly Lys Glu Thr Arg Glu Ile Asp Gly Arg Gln Tyr
            130                 135                 140

Val Leu Glu Met Pro Leu His Ala Asp Phe Ala Leu Ile Lys Ala Tyr
145                 150                 155                 160

Lys Gly Asp Arg Trp Gly Asn Leu Ile Tyr Arg Lys Ala Ala Arg Asn
            165                 170                 175

Phe Gly Pro Ile Met Ala Met Ala Ala Lys Thr Ala Ile Ala Gln Val
            180                 185                 190

Asp Gln Ile Val Glu Leu Gly Glu Leu Asp Pro Glu His Ile Ile Thr
            195                 200                 205

Pro Gly Ile Phe Val Gln Arg Val Ala Val Thr Gly Ala Ala Ser
            210                 215                 220

Ser Ile Ala Met Thr Ile Thr Thr Lys Leu Ser Arg Thr Gln Met Ala
225                 230                 235                 240

Gln Arg Val Ala Ala Asp Ile Gln Glu Gly Ala Tyr Val Asn Leu Gly
            245                 250                 255

Ile Gly Ala Pro Thr Leu Val Ala Asn Phe Leu Gly Asp Lys Glu Val
            260                 265                 270
```

```
Phe Leu His Ser Glu Asn Gly Leu Gly Met Gly Pro Ser Pro Ala
            275                 280                 285

Pro Gly Glu Glu Asp Asp Leu Ile Asn Ala Gly Lys Gln His Val
        290                 295                 300

Thr Leu Leu Thr Gly Gly Ala Phe Phe His His Ala Asp Ser Phe Ser
305                 310                 315                 320

Met Met Arg Gly Gly His Leu Asp Ile Ala Val Leu Gly Ala Phe Gln
                325                 330                 335

Val Ser Val Lys Gly Asp Leu Ala Asn Trp His Thr Gly Ala Glu Gly
            340                 345                 350

Ser Ile Pro Ala Val Gly Gly Ala Met Asp Leu Ala Thr Gly Ala Arg
        355                 360                 365

Gln Val Phe Val Met Met Asp His Leu Thr Lys Ser Gly Glu Ser Lys
    370                 375                 380

Ile Val Pro Glu Cys Thr Tyr Pro Leu Thr Gly Ile Gly Cys Val Ser
385                 390                 395                 400

Arg Ile Tyr Thr Asp Leu Ala Val Leu Glu Val Thr Ser Asp Gly Leu
                405                 410                 415

Lys Val Val Glu Ile Cys Ala Asp Ile Asp Phe Asp Glu Leu Gln Lys
            420                 425                 430

Leu Ser Gly Val Pro Leu Ile Lys
        435                 440

<210> SEQ ID NO 7
<211> LENGTH: 524
<212> TYPE: PRT
<213> ORGANISM: Clostridium propionicum

<400> SEQUENCE: 7

Met Arg Lys Val Pro Ile Ile Thr Ala Asp Glu Ala Ala Lys Leu Ile
1               5                   10                  15

Lys Asp Gly Asp Thr Val Thr Thr Ser Gly Phe Val Gly Asn Ala Ile
            20                  25                  30

Pro Glu Ala Leu Asp Arg Ala Val Glu Lys Arg Phe Leu Glu Thr Gly
        35                  40                  45

Glu Pro Lys Asn Ile Thr Tyr Val Tyr Cys Gly Ser Gln Gly Asn Arg
    50                  55                  60

Asp Gly Arg Gly Ala Glu His Phe Ala His Glu Gly Leu Leu Lys Arg
65                  70                  75                  80

Tyr Ile Ala Gly His Trp Ala Thr Val Pro Ala Leu Gly Lys Met Ala
                85                  90                  95

Met Glu Asn Lys Met Glu Ala Tyr Asn Val Ser Gln Gly Ala Leu Cys
            100                 105                 110

His Leu Phe Arg Asp Ile Ala Ser His Lys Pro Gly Val Phe Thr Lys
        115                 120                 125

Val Gly Ile Gly Thr Phe Ile Asp Pro Arg Asn Gly Gly Gly Lys Val
    130                 135                 140

Asn Asp Ile Thr Lys Glu Asp Ile Val Glu Leu Val Glu Ile Lys Gly
145                 150                 155                 160

Gln Glu Tyr Leu Phe Tyr Pro Ala Phe Pro Ile His Val Ala Leu Ile
                165                 170                 175

Arg Gly Thr Tyr Ala Asp Glu Ser Gly Asn Ile Thr Phe Glu Lys Glu
            180                 185                 190

Val Ala Pro Leu Glu Gly Thr Ser Val Cys Gln Ala Val Lys Asn Ser
        195                 200                 205
```

```
Gly Gly Ile Val Val Gln Val Glu Arg Val Val Lys Ala Gly Thr
210                 215                 220

Leu Asp Pro Arg His Val Lys Val Pro Gly Ile Tyr Val Asp Tyr Val
225                 230                 235                 240

Val Val Ala Asp Pro Glu Asp His Gln Gln Ser Leu Asp Cys Glu Tyr
                245                 250                 255

Asp Pro Ala Leu Ser Gly Glu His Arg Arg Pro Glu Val Val Gly Glu
            260                 265                 270

Pro Leu Pro Leu Ser Ala Lys Lys Val Ile Gly Arg Arg Gly Ala Ile
        275                 280                 285

Glu Leu Glu Lys Asp Val Ala Val Asn Leu Gly Val Gly Ala Pro Glu
    290                 295                 300

Tyr Val Ala Ser Val Ala Asp Glu Gly Ile Val Asp Phe Met Thr
305                 310                 315                 320

Leu Thr Ala Glu Ser Gly Ala Ile Gly Gly Val Pro Ala Gly Gly Val
                325                 330                 335

Arg Phe Gly Ala Ser Tyr Asn Ala Asp Ala Leu Ile Asp Gln Gly Tyr
            340                 345                 350

Gln Phe Asp Tyr Tyr Asp Gly Gly Gly Leu Asp Leu Cys Tyr Leu Gly
        355                 360                 365

Leu Ala Glu Cys Asp Glu Lys Gly Asn Ile Asn Val Ser Arg Phe Gly
370                 375                 380

Pro Arg Ile Ala Gly Cys Gly Gly Phe Ile Asn Ile Thr Gln Asn Thr
385                 390                 395                 400

Pro Lys Val Phe Phe Cys Gly Thr Phe Thr Ala Gly Gly Leu Lys Val
                405                 410                 415

Lys Ile Glu Asp Gly Lys Val Ile Ile Val Gln Glu Gly Lys Gln Lys
            420                 425                 430

Lys Phe Leu Lys Ala Val Glu Gln Ile Thr Phe Asn Gly Asp Val Ala
        435                 440                 445

Leu Ala Asn Lys Gln Gln Val Thr Tyr Ile Thr Glu Arg Cys Val Phe
    450                 455                 460

Leu Leu Lys Glu Asp Gly Leu His Leu Ser Glu Ile Ala Pro Gly Ile
465                 470                 475                 480

Asp Leu Gln Thr Gln Ile Leu Asp Val Met Asp Phe Ala Pro Ile Ile
                485                 490                 495

Asp Arg Asp Ala Asn Gly Gln Ile Lys Leu Met Asp Ala Ala Leu Phe
            500                 505                 510

Ala Glu Gly Leu Met Gly Leu Lys Glu Met Lys Ser
        515                 520

<210> SEQ ID NO 8
<211> LENGTH: 246
<212> TYPE: PRT
<213> ORGANISM: Chromobacterium violaceum

<400> SEQUENCE: 8

Met Lys Gln Gln Glu Val Arg Gln Arg Ala Phe Ala Met Pro Leu Thr
1                5                  10                  15

Ser Pro Ala Phe Pro Pro Gly Tyr Arg Phe Val Asn Arg Glu Tyr
            20                  25                  30

Met Ile Ile Thr Tyr Arg Thr Asp Pro Ala Ala Ile Glu Ala Val Leu
        35                  40                  45

Pro Glu Pro Leu Gln Met Ala Glu Pro Val Val Arg Tyr Glu Phe Ile
    50                  55                  60
```

```
Arg Met Pro Asp Ser Thr Gly Phe Gly Asp Tyr Ser Glu Ser Gly Gln
 65                  70                  75                  80

Val Ile Pro Val Thr Phe Arg Gly Glu Arg Gly Ser Tyr Thr Leu Ala
                 85                  90                  95

Met Phe Leu Asp Asp Gln Pro Pro Leu Ala Gly Gly Arg Glu Leu Trp
            100                 105                 110

Gly Phe Pro Lys Lys Ala Gly Lys Pro Arg Leu Glu Val His Gln Asp
            115                 120                 125

Thr Leu Val Gly Ser Leu Asp Phe Gly Pro Val Arg Ile Ala Thr Gly
            130                 135                 140

Thr Met Gly Tyr Lys Tyr Glu Ala Leu Asp Arg Ser Ala Leu Leu Ala
145                 150                 155                 160

Ser Leu Ala Glu Pro Asn Phe Leu Leu Lys Ile Ile Pro His Val Asp
                165                 170                 175

Gly Ser Pro Arg Ile Cys Glu Leu Val Arg Tyr His Thr Thr Asp Val
                180                 185                 190

Ala Ile Lys Gly Ala Trp Ser Ala Pro Gly Ser Leu Glu Leu His Pro
            195                 200                 205

His Ala Leu Ala Pro Val Ala Ala Leu Pro Val Leu Glu Val Leu Ser
210                 215                 220

Ala Arg His Phe Val Cys Asp Leu Thr Leu Asp Leu Gly Thr Val Val
225                 230                 235                 240

Phe Asp Tyr Leu Arg Gln
                245

<210> SEQ ID NO 9
<211> LENGTH: 252
<212> TYPE: PRT
<213> ORGANISM: Lactobacillus brevis

<400> SEQUENCE: 9

Met Ser Asn Arg Leu Asp Gly Lys Val Ala Ile Ile Thr Gly Gly Thr
  1               5                  10                  15

Leu Gly Ile Gly Leu Ala Ile Ala Thr Lys Phe Val Glu Glu Gly Ala
             20                  25                  30

Lys Val Met Ile Thr Gly Arg His Ser Asp Val Gly Glu Lys Ala Ala
         35                  40                  45

Lys Ser Val Gly Thr Pro Asp Gln Ile Gln Phe Phe Gln His Asp Ser
     50                  55                  60

Ser Asp Glu Asp Gly Trp Thr Lys Leu Phe Asp Ala Thr Glu Lys Ala
 65                  70                  75                  80

Phe Gly Pro Val Ser Thr Leu Val Asn Asn Ala Gly Ile Ala Val Asn
                 85                  90                  95

Lys Ser Val Glu Glu Thr Thr Thr Ala Glu Trp Arg Lys Leu Leu Ala
            100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Ile
            130                 135                 140

Glu Gly Phe Val Gly Asp Pro Ser Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
                180                 185                 190
```

```
Thr Pro Leu Val Asp Asp Leu Pro Gly Ala Glu Ala Met Ser Gln
        195                 200                 205

Arg Thr Lys Thr Pro Met Gly His Ile Gly Glu Pro Asn Asp Ile Ala
    210                 215                 220

Tyr Ile Cys Val Tyr Leu Ala Ser Asn Glu Ser Lys Phe Ala Thr Gly
225                 230                 235                 240

Ser Glu Phe Val Val Asp Gly Gly Tyr Thr Ala Gln
                245                 250

<210> SEQ ID NO 10
<211> LENGTH: 244
<212> TYPE: PRT
<213> ORGANISM: Clostridium acetobutylicum

<400> SEQUENCE: 10

Met Leu Lys Asp Glu Val Ile Lys Gln Ile Ser Thr Pro Leu Thr Ser
1               5                   10                  15

Pro Ala Phe Pro Arg Gly Pro Tyr Lys Phe His Asn Arg Glu Tyr Phe
                20                  25                  30

Asn Ile Val Tyr Arg Thr Asp Met Asp Ala Leu Arg Lys Val Val Pro
            35                  40                  45

Glu Pro Leu Glu Ile Asp Glu Pro Leu Val Arg Phe Glu Ile Met Ala
    50                  55                  60

Met His Asp Thr Ser Gly Leu Gly Cys Tyr Thr Glu Ser Gly Gln Ala
65                  70                  75                  80

Ile Pro Val Ser Phe Asn Gly Val Lys Gly Asp Tyr Leu His Met Met
                85                  90                  95

Tyr Leu Asp Asn Glu Pro Ala Ile Ala Val Gly Arg Glu Leu Ser Ala
            100                 105                 110

Tyr Pro Lys Lys Leu Gly Tyr Pro Lys Leu Phe Val Asp Ser Asp Thr
    115                 120                 125

Leu Val Gly Thr Leu Asp Tyr Gly Lys Leu Arg Val Ala Thr Ala Thr
130                 135                 140

Met Gly Tyr Lys His Lys Ala Leu Asp Ala Asn Glu Ala Lys Asp Gln
145                 150                 155                 160

Ile Cys Arg Pro Asn Tyr Met Leu Lys Ile Ile Pro Asn Tyr Asp Gly
                165                 170                 175

Ser Pro Arg Ile Cys Glu Leu Ile Asn Ala Lys Ile Thr Asp Val Thr
            180                 185                 190

Val His Glu Ala Trp Thr Gly Pro Thr Arg Leu Gln Leu Phe Asp His
    195                 200                 205

Ala Met Ala Pro Leu Asn Asp Leu Pro Val Lys Glu Ile Val Ser Ser
210                 215                 220

Ser His Ile Leu Ala Asp Ile Ile Leu Pro Arg Ala Glu Val Ile Tyr
225                 230                 235                 240

Asp Tyr Leu Lys

<210> SEQ ID NO 11
<211> LENGTH: 351
<212> TYPE: PRT
<213> ORGANISM: Clostridium beijerinckii
```

<400> SEQUENCE: 11

```
Met Lys Gly Phe Ala Met Leu Gly Ile Asn Lys Leu Gly Trp Ile Glu
1               5                   10                  15

Lys Glu Arg Pro Val Ala Gly Ser Tyr Asp Ala Ile Val Arg Pro Leu
            20                  25                  30

Ala Val Ser Pro Cys Thr Ser Asp Ile His Thr Val Phe Glu Gly Ala
        35                  40                  45

Leu Gly Asp Arg Lys Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Gly Glu Tyr Phe His Val Asn Asp
        115                 120                 125

Ala Asp Met Asn Leu Ala Ile Leu Pro Lys Asp Met Pro Leu Glu Asn
    130                 135                 140

Ala Val Met Ile Thr Asp Met Met Thr Thr Gly Phe His Gly Ala Glu
145                 150                 155                 160

Leu Ala Asp Ile Gln Met Gly Ser Ser Val Val Val Ile Gly Ile Gly
                165                 170                 175

Ala Val Gly Leu Met Gly Ile Ala Gly Ala Lys Leu Arg Gly Ala Gly
            180                 185                 190

Arg Ile Ile Gly Val Gly Ser Arg Pro Ile Cys Val Glu Ala Ala Lys
        195                 200                 205

Phe Tyr Gly Ala Thr Asp Ile Leu Asn Tyr Lys Asn Gly His Ile Val
    210                 215                 220

Asp Gln Val Met Lys Leu Thr Asn Gly Lys Gly Val Asp Arg Val Ile
225                 230                 235                 240

Met Ala Gly Gly Gly Ser Glu Thr Leu Ser Gln Ala Val Ser Met Val
                245                 250                 255

Lys Pro Gly Gly Ile Ile Ser Asn Ile Asn Tyr His Gly Ser Gly Asp
            260                 265                 270

Ala Leu Leu Ile Pro Arg Val Glu Trp Gly Cys Gly Met Ala His Lys
        275                 280                 285

Thr Ile Lys Gly Gly Leu Cys Pro Gly Gly Arg Leu Arg Ala Glu Met
    290                 295                 300

Leu Arg Asp Met Val Val Tyr Asn Arg Val Asp Leu Ser Lys Leu Val
305                 310                 315                 320

Thr His Val Tyr His Gly Phe Asp His Ile Glu Glu Ala Leu Leu Leu
                325                 330                 335

Met Lys Asp Lys Pro Lys Asp Leu Ile Lys Ala Val Val Ile Leu
            340                 345                 350
```

<210> SEQ ID NO 12
<211> LENGTH: 542
<212> TYPE: PRT
<213> ORGANISM: Cupriavidus necator

<400> SEQUENCE: 12

```
Met Lys Val Ile Thr Ala Arg Glu Ala Ala Ala Leu Val Gln Asp Gly
 1               5                  10                  15

Trp Thr Val Ala Ser Ala Gly Phe Val Gly Ala Gly His Ala Glu Ala
             20                  25                  30

Val Thr Glu Ala Leu Glu Gln Arg Phe Leu Gln Ser Gly Leu Pro Arg
         35                  40                  45

Asp Leu Thr Leu Val Tyr Ser Ala Gly Gln Gly Asp Arg Gly Ala Arg
     50                  55                  60

Gly Val Asn His Phe Gly Asn Ala Gly Met Thr Ala Ser Ile Val Gly
 65                  70                  75                  80

Gly His Trp Arg Ser Ala Thr Arg Leu Ala Thr Leu Ala Met Ala Glu
                 85                  90                  95

Gln Cys Glu Gly Tyr Asn Leu Pro Gln Gly Val Leu Thr His Leu Tyr
            100                 105                 110

Arg Ala Ile Ala Gly Gly Lys Pro Gly Val Met Thr Lys Ile Gly Leu
        115                 120                 125

His Thr Phe Val Asp Pro Arg Thr Ala Gln Asp Ala Arg Tyr His Gly
    130                 135                 140

Gly Ala Val Asn Glu Arg Ala Arg Gln Ala Ile Ala Glu Gly Lys Ala
145                 150                 155                 160

Cys Trp Val Asp Ala Val Asp Phe Arg Gly Asp Glu Tyr Leu Phe Tyr
                165                 170                 175

Pro Ser Phe Pro Ile His Cys Ala Leu Ile Arg Cys Thr Ala Ala Asp
            180                 185                 190

Ala Arg Gly Asn Leu Ser Thr His Arg Glu Ala Phe His His Glu Leu
        195                 200                 205

Leu Ala Met Ala Gln Ala His Asn Ser Gly Ile Val Ile Ala
    210                 215                 220

Gln Val Glu Ser Leu Val Asp His His Glu Ile Leu Gln Ala Ile His
225                 230                 235                 240

Val Pro Gly Ile Leu Val Asp Tyr Val Val Val Cys Asp Asn Pro Ala
                245                 250                 255

Asn His Gln Met Thr Phe Ala Glu Ser Tyr Asn Pro Ala Tyr Val Thr
            260                 265                 270

Pro Trp Gln Gly Glu Ala Ala Val Ala Glu Ala Glu Ala Ala Pro Val
        275                 280                 285

Ala Ala Gly Pro Leu Asp Ala Arg Thr Ile Val Gln Arg Arg Ala Val
    290                 295                 300

Met Glu Leu Ala Arg Arg Ala Pro Arg Val Val Asn Leu Gly Val Gly
305                 310                 315                 320

Met Pro Ala Ala Val Gly Met Leu Ala His Gln Ala Gly Leu Asp Gly
                325                 330                 335

Phe Thr Leu Thr Val Glu Ala Gly Pro Ile Gly Gly Thr Pro Ala Asp
            340                 345                 350

Gly Leu Ser Phe Gly Ala Ser Ala Tyr Pro Glu Ala Val Val Asp Gln
        355                 360                 365

Pro Ala Gln Phe Asp Phe Tyr Glu Gly Gly Ile Asp Leu Ala Ile
    370                 375                 380

Leu Gly Leu Ala Glu Leu Asp Gly His Gly Asn Val Asn Val Ser Lys
385                 390                 395                 400

Phe Gly Glu Gly Glu Gly Ala Ser Ile Ala Gly Val Gly Gly Phe Ile
                405                 410                 415
```

-continued

Asn Ile Thr Gln Ser Ala Arg Ala Val Val Phe Met Gly Thr Leu Thr
            420                 425                 430

Ala Gly Gly Leu Glu Val Arg Ala Gly Asp Gly Gly Leu Gln Ile Val
            435                 440                 445

Arg Glu Gly Arg Val Lys Lys Ile Val Pro Glu Val Ser His Leu Ser
450                 455                 460

Phe Asn Gly Pro Tyr Val Ala Ser Leu Gly Ile Pro Val Leu Tyr Ile
465                 470                 475                 480

Thr Glu Arg Ala Val Phe Glu Met Arg Ala Gly Ala Asp Gly Glu Ala
                485                 490                 495

Arg Leu Thr Leu Val Glu Ile Ala Pro Gly Val Asp Leu Gln Arg Asp
            500                 505                 510

Val Leu Asp Gln Cys Ser Thr Pro Ile Ala Val Ala Gln Asp Leu Arg
            515                 520                 525

Glu Met Asp Ala Arg Leu Phe Gln Ala Gly Pro Leu His Leu
        530                 535                 540

<210> SEQ ID NO 13
<211> LENGTH: 438
<212> TYPE: PRT
<213> ORGANISM: Clostridium aminobutyricum

<400> SEQUENCE: 13

Met Asp Trp Lys Lys Ile Tyr Glu Asp Arg Thr Cys Thr Ala Asp Glu
1               5                   10                  15

Ala Val Lys Ser Ile Lys Ser Gly Asp Arg Val Leu Phe Ala His Cys
            20                  25                  30

Val Ala Glu Pro Pro Val Leu Val Glu Ala Met Val Ala Asn Ala Ala
        35                  40                  45

Ala Tyr Lys Asn Val Thr Val Ser His Met Val Thr Leu Gly Lys Gly
    50                  55                  60

Glu Tyr Ser Lys Pro Glu Tyr Lys Glu Asn Phe Thr Phe Glu Gly Trp
65                  70                  75                  80

Phe Thr Ser Pro Ser Thr Arg Gly Ser Ile Ala Glu Gly His Gly Gln
                85                  90                  95

Phe Val Pro Val Phe His Glu Val Pro Ser Leu Ile Arg Lys Asp
            100                 105                 110

Ile Phe His Val Asp Val Phe Met Val Met Val Ser Pro Pro Asp His
        115                 120                 125

Asn Gly Phe Cys Cys Val Gly Val Ser Ser Asp Tyr Thr Met Gln Ala
    130                 135                 140

Ile Lys Ser Ala Lys Ile Val Leu Ala Glu Val Asn Asp Gln Val Pro
145                 150                 155                 160

Val Val Tyr Gly Asp Thr Phe Val His Val Ser Glu Ile Asp Lys Phe
                165                 170                 175

Val Glu Thr Ser His Pro Leu Pro Glu Ile Gly Leu Pro Lys Ile Gly
            180                 185                 190

Glu Val Glu Ala Ala Ile Gly Lys His Cys Ala Ser Leu Ile Glu Asp
        195                 200                 205

Gly Ser Thr Leu Gln Leu Gly Ile Gly Ala Ile Pro Asp Ala Val Leu
    210                 215                 220

Ser Gln Leu Lys Asp Lys Lys His Leu Gly Ile His Ser Glu Met Ile
225                 230                 235                 240

Ser Asp Gly Val Val Asp Leu Tyr Glu Ala Gly Val Ile Asp Cys Ser
                245                 250                 255

-continued

```
Gln Lys Ser Ile Asp Lys Gly Lys Met Ala Ile Thr Phe Leu Met Gly
            260                 265                 270

Thr Lys Arg Leu Tyr Asp Phe Ala Ala Asn Asn Pro Lys Val Glu Leu
        275                 280                 285

Lys Pro Val Asp Tyr Ile Asn His Pro Ser Val Val Ala Gln Cys Ser
    290                 295                 300

Lys Met Val Cys Ile Asn Ala Cys Leu Gln Val Asp Phe Met Gly Gln
305                 310                 315                 320

Ile Val Ser Asp Ser Ile Gly Thr Lys Gln Phe Ser Gly Val Gly Gly
                325                 330                 335

Gln Val Asp Phe Val Arg Gly Ala Ser Met Ser Ile Asp Gly Lys Gly
            340                 345                 350

Lys Ala Ile Ile Ala Met Pro Ser Val Ala Lys Lys Lys Asp Gly Ser
        355                 360                 365

Met Ile Ser Lys Ile Val Pro Phe Ile Asp His Gly Ala Ala Val Thr
    370                 375                 380

Thr Ser Arg Asn Asp Ala Asp Tyr Val Val Thr Glu Tyr Gly Ile Ala
385                 390                 395                 400

Glu Met Lys Gly Lys Ser Leu Gln Asp Arg Ala Arg Ala Leu Ile Asn
                405                 410                 415

Ile Ala His Pro Asp Phe Lys Asp Glu Leu Lys Ala Glu Phe Glu Lys
            420                 425                 430

Arg Phe Asn Ala Ala Phe
            435

<210> SEQ ID NO 14
<211> LENGTH: 132
<212> TYPE: PRT
<213> ORGANISM: Escherichia coli

<400> SEQUENCE: 14

Met Ser Thr Thr His Asn Val Pro Gln Gly Asp Leu Val Leu Arg Thr
1               5                   10                  15

Leu Ala Met Pro Ala Asp Thr Asn Ala Asn Gly Asp Ile Phe Gly Gly
            20                  25                  30

Trp Leu Met Ser Gln Met Asp Ile Gly Gly Ala Ile Leu Ala Lys Glu
        35                  40                  45

Ile Ala His Gly Arg Val Val Thr Val Arg Val Glu Gly Met Thr Phe
    50                  55                  60

Leu Arg Pro Val Ala Val Gly Asp Val Val Cys Cys Tyr Ala Arg Cys
65                  70                  75                  80

Val Gln Lys Gly Thr Thr Ser Val Ser Ile Asn Ile Glu Val Trp Val
                85                  90                  95

Lys Lys Val Ala Ser Glu Pro Ile Gly Gln Arg Tyr Lys Ala Thr Glu
            100                 105                 110

Ala Leu Phe Lys Tyr Val Ala Val Asp Pro Glu Gly Lys Pro Arg Ala
        115                 120                 125

Leu Pro Val Glu
    130
```

BIOSYNTHESIS OF 1,3-BUTANEDIOL

TECHNICAL FIELD

This invention provides o methods for biosynthesizing 3-oxo-5-hydroxypentanoyl-CoA using a polypeptide having β-ketothiolase activity, and enzymatically converting 3-oxo-5-hydroxypentanoyl-CoA to 1,3-butanediol (1,3-BDO; also known as 1,3-butylene glycol) using one or more polypeptide having CoA transferase, thioesterase, decarboxylase, or secondary alcohol dehydrogenase activity, or recombinant host cells expressing one or more of such enzymes.

BACKGROUND 1,3-BDO is used for a wide variety of purposes, serving as a starter unit for the production of various compounds such as fragrances, pheromones, insecticides, penems and carbapenems. 1,3-BDO typically may be chemically produced by (1) hydrogenation of 4-hydroxy-2-butanone using ruthenium complexes of phosphine-aminophosphine and (2) from threonine by nitrous deamination in the presence of bromide ion followed by esterification and reduction. However, the methods typically are energy intensive, involve multiple steps, consume large amounts of solvent and/or produce large amounts of by-products, thus limiting large-scale production. In particular, these methods are not economical for the large-scale production of 1,3-butadiene via catalytic dehydration of 1,3-BDO. Accordingly, it is clear that there is a need for sustainable and efficient methods for producing 1,3-BDO.

SUMMARY

This document is based at least in part on the discovery that it is possible to construct biochemical pathways for using, inter alia, a β-ketothiolase to produce 3-oxo-5-hydroxypentanoyl-CoA, which can be converted in one or more enzymatic steps to 1,3-BDO using, for example, a CoA transferase or a thioesterase, a decarboxylase, and/or a secondary alcohol dehydrogenase.

In one aspect, this document features a method of producing 3-oxo-5-hydroxypentanoyl-CoA. The method includes enzymatically converting 3-hydroxypropionyl-CoA to 3-oxo-5-hydroxypentanoyl-CoA using a β-ketothiolase classified under EC. 2.3.1.- (e.g., EC 2.3.1.16 or EC 2.3.1.174). The β-ketothiolase can have at least 70% sequence identity to the amino acid sequence set forth in SEQ ID NOs: 1 or 2. The method further can include enzymatically converting 3-oxo-5-hydroxypentanoyl-CoA to 1,3-butanediol using a thioesterase or a CoA transferase, a decarboxylase, and a secondary alcohol dehydrogenase. The thioesterase can be classified under EC 3.1.2.-. For example, the thioesterase can have at least 70% sequence identity to the amino acid sequence set forth in SEQ ID NO: 3. The CoA transferase can be classified under EC 2.8.3.-. For example, the CoA transferase can have at least 70% sequence identity to the amino acid sequence set forth in SEQ ID NO: 5, 6, or 12. The decarboxylase can be classified under EC 4.1.1.4. For example, the decarboxylase can have at least 70% sequence identity to the amino acid sequence set forth in SEQ ID NO: 8 or 10. The secondary alcohol dehydrogenase can be classified under EC 1.1.1.B3, EC 1.1.1.B4, or EC 1.1.1.80. The secondary alcohol dehydrogenase can have at least 70% sequence identity to the amino acid sequence set forth in SEQ ID NO:4, 9, or 11.

This document also features a method for biosynthesizing 1,3-butanediol. The method includes enzymatically synthesizing 3-oxo-5-hydroxypentanoyl-CoA from 3-hydroxypropionyl-CoA using a β-ketothiolase classified under EC. 2.3.1.- and enzymatically converting 3-oxo-5-hydroxypentanoyl-CoA to 1,3-butanediol. The β-ketothiolase can have at least 70% sequence identity to the amino acid sequence set forth in SEQ ID NOs:1 or 2. The 3-oxo-5-hydroxypentanoyl-CoA can be converted to 3-oxo-5-hydroxypentanoate using a CoA transferase or a thioesterase, 3-oxo-5-hydroxypentanoate can be converted to 4-hydroxybutan-2-one using a decarboxylase, and 4-hydroxybutan-2-one can be converted to 1,3-butanediol using a secondary alcohol dehydrogenase. The thioesterase can have at least 70% sequence identity to the amino acid sequence set forth in SEQ ID NO: 3. The secondary alcohol dehydrogenase can have at least 70% sequence identity to the amino acid sequence set forth in SEQ ID NO:4, 9, or 11. The decarboxylase can have at least 70% sequence identity to the amino acid sequence set forth in SEQ ID NO: 8 or 10. The CoA transferase can have at least 70% sequence identity to the amino acid sequence set forth in SEQ ID NO: 5 or 6.

In any of the methods, 3-hydroxypropionyl-CoA can be enzymatically produced from malonyl-CoA. For example, 3-hydroxypropionyl-CoA can be enzymatically produced from malonyl-CoA using one or more of a malonyl-CoA reductase, a 3-hydroxypropionate dehydrogenase, a CoA transferase, and a 3-hydroxypropionyl-CoA synthase.

Any of the methods can be performed in a recombinant host. In some embodiments, the host is retained using a ceramic membrane. In some embodiments, the cultivation strategy entails achieving anaerobic, micro-aerobic, or aerobic cultivation conditions. In some embodiments, the cultivation strategy includes limiting nutrients, such as limiting nitrogen, phosphate or oxygen.

In any of the methods, the principal carbon source fed to the fermentation can derive from a biological feedstock. For example, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

In any of the methods, the principal carbon source fed to the fermentation can derive from a non-biological feedstock. For example, the non-biological feedstock can be or can derive from natural gas, syngas, $CO_2/H_2$, methanol, ethanol, benzoate, non-volatile residue (NVR) or a caustic wash waste stream from cyclohexane oxidation processes, or terephthalic acid/isophthalic acid mixture waste streams.

In some embodiments, the host microorganism's tolerance to high concentrations of 1,3-BDO is improved through continuous cultivation in a selective environment.

This document also features a recombinant host that includes at least one exogenous nucleic acid encoding (i) a β-ketothiolase, (ii) a secondary alcohol dehydrogenase and one or more of (iii) a decarboxylase, and (iv) a thioesterase or a CoA transferase, the host producing 1,3-butanediol. The host further can include one or more of the following exogenous enzymes: (v) a malonyl-CoA reductase, (vi) a 3-hydroxypropionate dehydrogenase, and (vii) a propionate CoA-transferase or a 3-hydroxypropionyl-CoA synthase. The β-ketothiolase can have at least 70% sequence identity to the amino acid sequence set forth in SEQ ID NOs: 1 or 2. The secondary alcohol dehydrogenase can have at least 70% sequence identity to the amino acid sequence set forth in SEQ ID NO:4, 9, or 11. The decarboxylase can have at least 70% sequence identity to the amino acid sequence set forth in SEQ ID NO: 8 or 10. The thioesterase can have at least 70% sequence identity to the amino acid sequence set forth in SEQ ID NO: 3. The CoA transferase can have at least 70% sequence identity to the amino acid sequence set forth in SEQ ID NO: 5, 6, 7 or 12.

In some embodiments, the host microorganism's biochemical network is attenuated or augmented to (1) ensure the intracellular availability of malonyl-CoA or acetyl-CoA, (2) create an NADH or NADPH imbalance that may only be balanced via the formation of one or more building blocks leading to 1,3-BDO production, (3) prevent degradation of central metabolites, central precursors leading to 1,3-BDO production and (4) ensure efficient efflux from the cell.

Any of the recombinant hosts can be a prokaryote such as a prokaryote from a genus selected from the group consisting of *Escherichia*; Clostridia; Corynebacteria; *Cupriavidus*; *Pseudomonas*; *Delftia*; *Bacillus*; *Lactobacillus*; *Lactococcus*; and *Rhodococcus*. For example, the prokaryote can be selected from the group consisting of *Escherichia coli*, *Clostridium ljungdahlii*, *Clostridium autoethanogenum*, *Clostridium kluyveri*, *Corynebacterium glutamicum*, *Cupriavidus necator*, *Cupriavidus metallidurans*. *Pseudomonas fluorescens*, *Pseudomonas putida*, *Pseudomonas oleavorans*, *Delftia acidovorans*, *Bacillus subtillis*, *Lactobacillus delbrueckii*, *Lactococcus lactis*, and *Rhodococcus equi*. Such prokaryotes also can be sources of genes for constructing recombinant host cells described herein that are capable of producing 1,3-BDO.

Any of the recombinant hosts can be a eukaryote such as a eukaryote from a genus selected from the group consisting of *Aspergillus*, *Saccharomyces*, *Pichia*, *Yarrowia*, *Issatchenkia*, *Debaryomyces*, *Arxula*, and *Kluyveromyces*. For example, the eukaryote can be selected from the group consisting of *Aspergillus niger*, *Saccharomyces cerevisiae*, *Pichia pastoris*, *Yarrowia lipolytica*, *Issathenkia orientalis*, *Debaryomyces hansenii*, *Arxula adenoinivorans*, and *Kluyveromyces lactis*. Such eukaryotes also can be sources of genes for constructing recombinant host cells described herein that are capable of producing 1,3-BDO.

Any of the recombinant hosts described herein further can include attenuations to one or more of the following enzymes: a polyhydroxyalkanoate synthase, an acetyl-CoA thioesterase, a phosphotransacetylase forming acetate, an acetate kinase, a lactate dehydrogenase, a menaquinol-fumarate oxidoreductase, an alcohol dehydrogenase forming ethanol, a triose phosphate isomerase, a pyruvate decarboxylase, a glucose-6-phosphate isomerase, NAD(P)H-consuming transhydrogenase, an NAD(P)H-specific glutamate dehydrogenase, or a NAD(P)H-utilizing glutamate.

Any of the recombinant hosts described herein further can overexpress one or more genes encoding: an acetyl-CoA synthetase, a 6-phosphogluconate dehydrogenase; a transketolase; a puridine nucleotide transhydrogenase; a glyceraldehyde-3P-dehydrogenase; a malic enzyme; a glucose-6-phosphate dehydrogenase; a glucose dehydrogenase; a fructose 1,6 diphosphatase; a L-alanine dehydrogenase; a L-glutamate dehydrogenase; a formate dehydrogenase; and/or a L-glutamine synthetase.

Many of the enzymes described herein catalyze reversible reactions, and the reaction of interest may be the reverse of the described reaction. The schematic pathways shown in FIG. 1 illustrate the reaction of interest for each of the intermediates.

In one aspect, this document features a method for producing a bioderived four carbon compound. The method for producing a bioderived four carbon compound can include culturing or growing a recombinant host as described herein under conditions and for a sufficient period of time to produce the bioderived four carbon compound, wherein, optionally, the bioderived four carbon compound is 1,3-butanediol.

In one aspect, this document features composition comprising a bioderived four carbon compound as described herein and a compound other than the bioderived four carbon compound, wherein the bioderived four carbon compound is 1,3-butanediol. For example, the bioderived four carbon compound is a cellular portion of a host cell or an organism.

This document also features a biobased polymer comprising the bioderived 1,3-butanediol.

This document also features a biobased resin comprising the bioderived 1,3-butanediol, as well as a molded product obtained by molding a biobased resin.

In another aspect, this document features a process for producing a biobased polymer that includes chemically reacting the bioderived 1,3-butanediol, with itself or another compound in a polymer producing reaction.

In another aspect, this document features a process for producing a biobased resin that includes chemically reacting the bioderived 1,3-butanediol, with itself or another compound in a resin producing reaction.

Also, described herein is a biochemical network comprising a polypeptide having β-ketothiolase activity, wherein the polypeptide having β-ketothiolase activity enzymatically converts 3-hydroxypropionyl-CoA to 3-oxo-5-hydroxypentanoyl-CoA.

The biochemical network can further include a polypeptide having thioesterase activity or a polypeptide having CoA transferase activity, a polypeptide having decarboxylase activity, and a polypeptide having secondary alcohol dehydrogenase activity. In one aspect, the biochemical network is a non-naturally occurring biochemical network comprising at least one substrate of FIG. 1, at least one exogenous nucleic acid encoding a polypeptide having the activity of at least one enzyme of FIG. 1 and at least one product of FIG. 1. In another aspect of the invention, the biochemical network is a non-naturally occurring biochemical network comprising a 3-hydroxypropionyl-CoA, an exogenous nucleic acid encoding a polypeptide having the activity of a β-ketothiolase classified under EC. 2.3.1 and a 3-hydroxypropionyl-CoA.

In one aspect of the invention, described is a step for forming at least one compound of FIG. 1. In one aspect of the invention, described is a means for forming at least one compound of FIG. 1.

In some aspects, the disclosure provides nucleic acid constructs and/or expression vectors comprising a polynucleotide encoding a polypeptide having β-ketothiolase activity, wherein the polynucleotide is operably linked to one or more heterologous control sequences that direct production of the polypeptide and wherein the polypeptide having β-ketothiolase activity is selected from the group consisting of: (a) a polypeptide having at least 70% sequence identity to the polypeptide of SEQ ID NOs: 1 or 2; a polynucleotide encoding a polypeptide having thioesterase activity, wherein the polynucleotide is operably linked to one or more heterologous control sequences that direct production of the polypeptide and wherein the polypeptide having thioesterase activity is selected from the group consisting of: (a) a polypeptide having at least 70% sequence identity to the polypeptide of SEQ ID NOs: 3 or 14; a polynucleotide encoding a polypeptide having CoA transferase activity, wherein the polynucleotide is operably linked to one or more heterologous control sequences that direct production of the polypeptide and wherein the polypeptide having CoA transferase activity is selected from the group consisting of: (a) a polypeptide having at least 70% sequence identity to the polypeptide of SEQ ID NOs:: 5, 6, 7, 12 or 13; a polynucleotide encoding a polypeptide having decarboxylase activity, wherein the polynucleotide is operably linked to one or more heterologous control sequences that direct production of the polypeptide and wherein the polypeptide having decarboxylase activity is selected from the group consisting of: (a) a polypeptide having at least 70% sequence identity to the polypeptide of SEQ ID NOs:: 8 or 10; or a polynucleotide encoding a polypeptide having secondary alcohol dehydrogenase, wherein the polynucleotide is operably linked to one or more heterologous control sequences that direct production of the polypeptide and wherein the polypeptide having secondary alcohol dehydrogenase activity is selected from the group consisting of: (a) a polypeptide having at least 70% sequence identity to the polypeptide of SEQ ID NOs:: 4, 9 or 11. The disclosure further provides compositions comprising the nucleic acid construct or expression vector as described above.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DESCRIPTION OF THE DRAWINGS

FIG. 2 contains the amino acid sequences of a *Cupriavidus necator* β-ketothiolase encoded by bktB (see GenBank Accession No. AAC38322.1, SEQ ID NO: 1), an *Escherichia coli* β-ketothiolase encoded by paaJ (see GenBank Accession No. AAC74479.1, SEQ ID NO: 2), an *Escherichia coli* thioesterase encoded by tesB (see GenBank Accession No. AAA24665.1, SEQ ID NO: 3), a *Micrococcus luteus* alcohol dehydrogenase (see GenBank Accession No. ADD83022.1, SEQ ID NO: 4); a *Escherichia coli* CoA-transferase encoded by atoAD (see Genbank Accession Nos. AAC75282.1 & AAC75281.1, SEQ ID NO: 5), a *Pseudomonas putida* CoA-transferase encoded by pcaIJ (see Genbank Accession Nos. ACA73091.1 & ACA73090.1, SEQ ID NO: 6), a *Clostridium propionicum* CoA-transferase encoded by ydiF (see Genbank Accession No. CAB77207.1, SEQ ID NO: 7), a *Chromobacterium violaceum* acetoacetate decarboxylase (see Genbank Accession No. AAQ61181.1, SEQ ID NO: 8), a *Lactobacillus brevis* alcohol dehydrogenase (see Genbank Accession No. CAD66648.1, SEQ ID NO: 9), a *Clostridium acetobutylicum* acetoacetate decarboxylase (Genbank Accession No. AAA63761.1, SEQ ID NO: 10), a *Clostridium beijerinckii* secondary alcohol dehydrogenase (see Genbank Accession No. AAA23199.2, SEQ ID NO: 11), a *Cupriavidus necator* CoA-transferase encoded by pct (see Genbank Accession No. CAJ93797.1, SEQ ID NO: 12), a *Clostridium aminobutyricum* CoA-transferase encoded by abfT (see Genbank Accession No. CAB60036.2, SEQ ID NO: 13) and an *Escherichia coli* thioesterase encoded by YciA (see Genbank Accession No. AAB60068.1, SEQ ID NO: 14).

DETAILED DESCRIPTION

Figure 1:
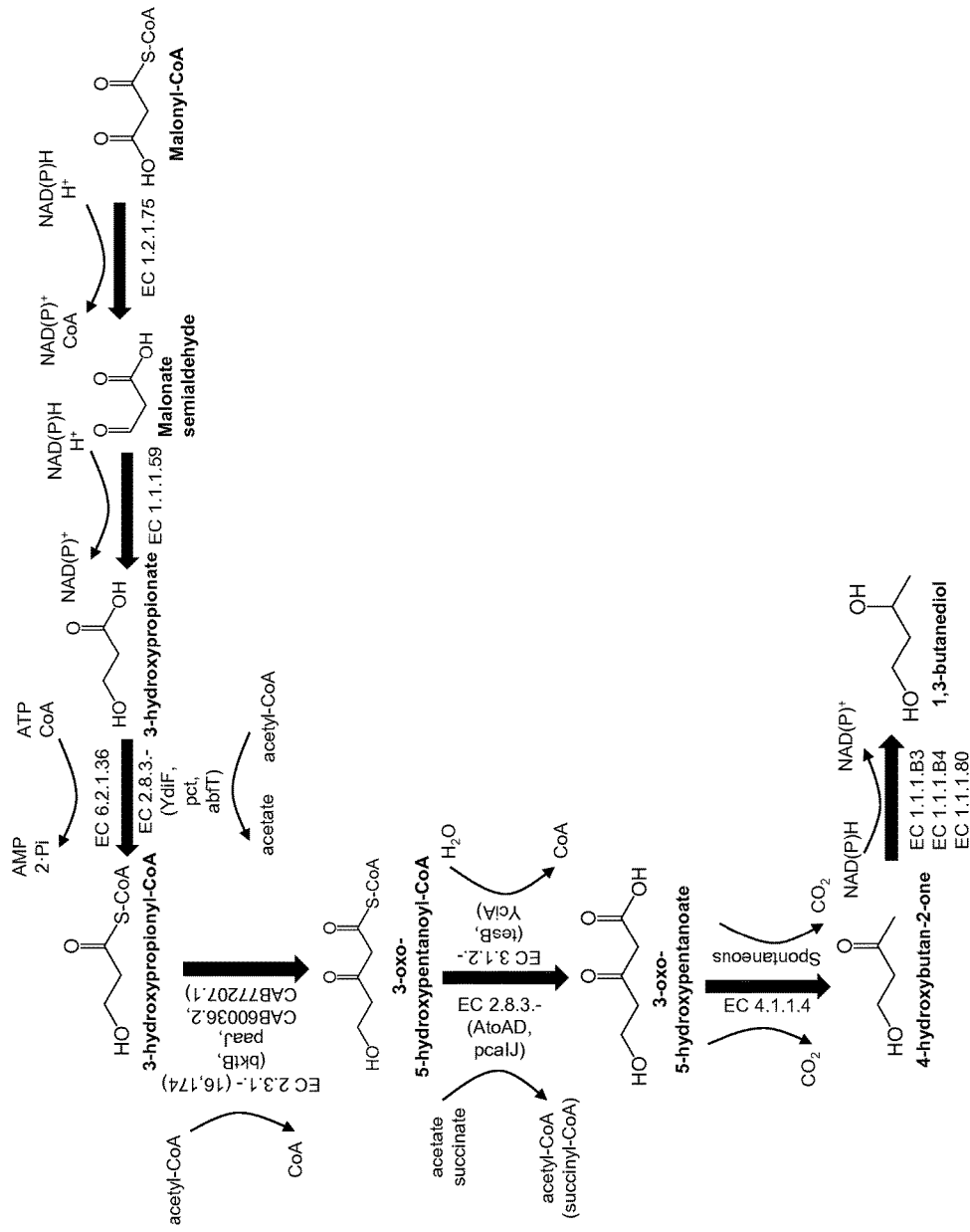
FIG. 1 is a schematic of an exemplary biochemical pathway leading to 1,3-BDO using malonyl-CoA as a central metabolite.

In general, this document provides enzymes, non-natural pathways, cultivation strategies, feedstocks, host microorganisms and attenuations to the host's biochemical network, for producing 3-oxo-5-hydroxypentanoyl-CoA, which can be converted in one or more enzymatic steps to 1,3-BDO. As used herein, the term "central precursor" is used to denote any metabolite in any metabolic pathway shown herein leading to the synthesis of 1,3-BDO. The term "central metabolite" is used herein to denote a metabolite that is produced in all microorganisms to support growth.

Host microorganisms described herein can include endogenous pathways that can be manipulated such that 1,3-BDO can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

For example, depending on the host and the compounds produced by the host, one or more of the following enzymes may be expressed in addition to a β-ketothiolase: a secondary alcohol dehydrogenase, a thioesterase, a CoA transferase, a decarboxylase, a malonyl-CoA reductase, a 3-hydroxypropionate dehydrogenase, or a 3-hydroxypropionyl-CoA synthase.

For example, a recombinant host can include an exogenous β-ketothiolase and produce 3-oxo-5-hydroxypentanoyl-CoA, which can be converted to 1,3-BDO.

For example, a recombinant host can include an exogenous β-ketothiolase, an exogenous thioesterase or an exogenous CoA transferase, an exogenous decarboxylase, and an exogenous secondary alcohol dehydrogenase, and produce 1,3-BDO. For example, a recombinant host can include an exogenous β-ketothiolase, an exogenous thioesterase, an exogenous decarboxylase, and an exogenous secondary alcohol dehydrogenase, and produce 1,3-BDO. For example, a recombinant host can include an exogenous β-ketothiolase, an exogenous CoA transferase, an exogenous decarboxylase, and an exogenous secondary alcohol dehydrogenase, and produce 1,3-BDO. Any of such hosts further can include one or more of a malonyl-CoA reductase, a 3-hydroxypropionate dehydrogenase, and a 3-hydroxypropionyl-CoA synthase (e.g., each of the malonyl-CoA reductase, the 3-hydroxypropionate dehydrogenase, and the 3-hydroxypropionyl-CoA synthase).

Within an engineered pathway, the enzymes can be from a single source, i.e., from one species or genera, or can be from multiple sources, i.e., different species or genera. Nucleic acids encoding the enzymes described herein have been identified from various organisms and are readily available in publicly available databases such as GenBank or EMBL.

As used herein, references to a particular enzyme (e.g. β-ketothiolase) means a polypeptide having the activity of the particular enzyme (e.g. a polypeptide having β-ketothiolase activity).

Any of the enzymes described herein that can be used for production of 1,3-BDO can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of the corresponding wild-type enzyme. It will be appreciated that the sequence identity can be determined on the basis of the mature enzyme (e.g., with any signal sequence removed) or on the basis of the immature enzyme (e.g., with any signal sequence included). It also will be appreciated that the initial methionine residue may or may not be present on any of the enzyme sequences described herein.

For example, a β-ketothiolase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Cupriavidus necator* (see GenBank Accession No. AAC38322.1, SEQ ID NO: 1) or an *Escherichia coli* (see GenBank Accession No. AAC74479.1, SEQ ID NO: 2) β-ketothiolase. See FIG. 2.

For example, a thioesterase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of an *Escherichia coli* thioesterase encoded by tesB (see GenBank Accession No. AAA24665.1, SEQ ID NO: 3) or YciA (see Genbank Accession No. AAB60068.1, SEQ ID NO: 14). See, FIG. 2.

For example, an alcohol dehydrogenase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Micrococcus luteus* secondary alcohol dehydrogenase (Genbank Accession No. ADD83022.1; SEQ ID NO: 4), a *Lactobacillus brevis* alcohol dehydrogenase (see Genbank Accession No. CAD66648.1, SEQ ID NO: 9) or a *Clostridium beijerinckii* secondary alcohol dehydrogenase (see Genbank Accession No. AAA23199.2, SEQ ID NO: 11). See, FIG. 2.

For example, an acetoacetate decarboxylase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Chromobacterium violaceum* acetoacetate decarboxylase (see Genbank Accession No. AAQ61181.1, SEQ ID NO: 8) or a *Clostridium acetobutylicum* acetoacetate decarboxylase (Genbank Accession No. AAA63761.1, SEQ ID NO: 10). See, FIG. 2.

For example, a CoA-transferase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of an *Escherichia coli* CoA-transferase encoded by atoAD (see Genbank Accession No. AAC75282.1 & AAC75281.1, SEQ ID NO: 5), a *Pseudomonas putida* CoA-transferase encoded by pcaIJ (see Genbank Accession No. ACA73091.1 & ACA73090.1, SEQ ID NO: 6), a *Clostridium propionicum* CoA-transferase encoded by ydiF (see Genbank Accession No. CAB77207.1, SEQ ID NO: 7), a *Cupriavidus necator* CoA-transferase encoded by pct (see Genbank Accession No. CAJ93797.1, SEQ ID NO: 12) a *Clostridium aminobutyricum* CoA-transferase encoded by abfT (see Genbank Accession No. CAB60036.2, SEQ ID NO: 13).

The percent identity (homology) between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagglutinin (HA), glutathione-S-transferase (GST), or maltose binding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Engineered hosts can naturally express none or some (e.g., one or more, two or more, three or more, four or more, five or more, or six or more) of the enzymes of the pathways described herein. Thus, a pathway within an engineered host can include all exogenous enzymes, or can include both endogenous and exogenous enzymes. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. As described herein recombinant hosts can include nucleic acids encoding one or more of a β-ketothiolase, a secondary alcohol dehydrogenase, a dehydrogenase, a decarboxylase, a synthase, a reductase, a thioesterase, or a CoA transferase, as described herein.

In addition, the production of 1,3-BDO can be performed in vitro using the isolated enzymes described herein, using a lysate (e.g., a cell lysate) from a host microorganism as a source of the enzymes, or using a plurality of lysates from different host microorganisms as the source of the enzymes.

The reactions of the pathways described herein can be performed in one or more host strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from of the above types of host cells and used in a purified or semi-purified form. Moreover, such extracts include lysates (e.g. cell lysates) that can be used as sources of relevant enzymes. In the methods provided by the document, all the steps can be performed in host cells, all the steps can be performed using extracted enzymes, or some of the steps can be performed in cells and others can be performed using extracted enzymes.

Enzymes Generating 1,3-Butanediol

As shown in FIG. 1, a β-ketothiolase, a secondary alcohol dehydrogenase, a CoA transferase, a thioesterase, and a decarboxylase can be used to produce 1,3-BDO from 3-hydroxypropionyl-CoA.

In some embodiments, a β-ketothiolase may be classified under EC 2.3.1.16, such as the gene product of bktB or may be classified under EC 2.3.1.174, such as the gene product of paaJ. The β-ketothiolase encoded by bktB from *Cupriavidus necator* accepts acetyl-CoA and propanoyl-CoA as substrates, forming a CoA-activated aliphatic backbone (see, e.g., Haywood et al., *FEMS Microbiology Letters*, 1988, 52:91-96; Slater et al., *J. Bacteriol.*, 1998, 180(8):1979-1987). Similarly, bktB from *Cupriavidus necator* accepts terminal hydroxylated substrates such as glycolate, forming a CoA-activated aliphatic backbone with terminal functionalization (Martin et al., *Nat. Commun.*, 2013, 4, 1414). The β-ketothiolase encoded by paaJ from *Escherichia coli* accepts succinyl-CoA and acetyl-CoA as substrates, forming a CoA-activated backbone with terminal functionalization (Nogales et al., *Microbiology*, 2007, 153, 357-365). Suitable β-ketothiolases can have at least 70% sequence identity to the amino acid sequence set forth in SEQ ID NO:1, SEQ ID NO:2, SEQ ID NO: 7 or SEQ ID NO: 13. See, FIG. 2.

In some embodiments, a thioesterase classified under EC 3.1.2.- or a CoA-transferase classified under, for example, EC 2.8.3.- (e.g., EC 2.8.3.6 or EC 2.8.3.8) such as the gene product of AtoAD or pcaIJ is used to hydrolyze the CoA moiety. For example, a suitable CoA-transferase can have at least 70% sequence identity to the amino acid sequence set forth in SEQ ID NO: 5 or SEQ ID NO: 6. See, FIG. 2.

The thioesterase can be the gene product of tesB (Cantu et al., *Protein Science*, 2010, 19, 1281-1295; Zhuang et al., *Biochemistry*, 2008, 47(9):2789-2796; Naggert et al., *J. Biol. Chem.*, 1991, 266(17):11044-11050). The thioesterase can be the gene product of YciA (Zhuang et al., *Biochemistry*, 2008, 47, 2789-2796), which accepts 3-ketoacyl-CoA substrates such as acetoacetyl-CoA for hydrolysis. For example, a suitable thioesterase can have at least 70% sequence identity to the amino acid sequence set forth in SEQ ID NO: 3 or SEQ ID NO. 14. See, FIG. 2.

An acetoacetate decarboxylase classified, for example, under EC 4.1.1.4 can be used to remove the carboxy group from 3-oxo-5-hydroxypentanoate to produce 4-hydroxybutan-2-one. For example, a suitable acetoacetate decarboxylase can have at least 70% sequence identity to the amino acid sequence set forth in SEQ ID NO: 8 or SEQ ID NO: 10. This reaction also can occur spontaneously.

An alcohol dehydrogenase (e.g., a secondary alcohol dehydrogenase) classified, for example, under EC 1.1.1.- such as EC 1.1.1.B3, EC 1.1.1.B4, or EC 1.1.1.80 can be used to produce 1,3-butanediol from 4-hydroxybutan-2-one. For example, a suitable secondary alcohol dehydrogenase can have at least 70% sequence identity to the amino acid sequence set forth in SEQ ID NO:4, SEQ ID NO: 9 or SEQ ID NO: 11. See, FIG. 2.

Pathway to 1,3-BDO

In some embodiments, 1,3-BDO is synthesized from the central metabolite, malonyl-CoA, by conversion of malonyl-CoA to malonate semialdehyde by a malonyl-CoA reductase classified, for example, under EC 1.2.1.75; followed by conversion of malonate semialdehyde to 3-hydroxypropionate by a 3-hydroxypropionate dehydrogenase classified, for example, under EC 1.1.1.59; followed by conversion of 3-hydroxypropionate to 3-hydroxypropionyl-CoA by a 3-hydroxypropionyl-CoA synthase classified, for example, under EC 6.2.1.36 or by a CoA-transferase classified, for example, under EC 2.8.3.- such as the gene product of YdiF (e.g., SEQ ID NO: 7), pct (e.g., SEQ ID NO: 12) or abfT (see Genbank Accession No. CAB60036.2, SEQ ID NO: 13); followed by conversion of 3-hydroxypropionyl-CoA to 3-oxo-5-hydroxypentanoyl-CoA using a β-ketothiolase classified, for example, under EC 2.3.1.16 or EC 2.3.1.174 such as the gene product of bktB or paaJ (e.g., SEQ ID NO: 1 or 2) or encoded by CAB60036.2 or CAB77207.1 (e.g., SEQ ID NO: 7 or 13); followed by conversion of 3-oxo-5-hydroxypentanoyl-CoA to 3-oxo-5-hydroxypentanoate by a CoA-transferase classified under, for example, EC 2.8.3.- such as the gene product of AtoAD from *E. coli* (e.g., SEQ ID NO: 5) or gene product of pcaIJ from *Pseudomonas putida* (e.g., SEQ ID NO: 6), or a thioesterase classified, for example, under EC 3.1.2.- such as the gene product of testB (e.g., SEQ ID NO: 3) or YciA (e.g., SEQ ID NO: 14); followed by conversion of 3-oxo-5-hydroxypentanoate to 4-hydroxybutan-2-one by an acetoacetate decarboxylase classified, for example, under EC 4.1.1.4 (e.g., SEQ ID NO: 8 or SEQ ID NO: 10); followed by conversion of 4-hydroxybutan-2-one to 1,3-BDO by a secondary alcohol dehydrogenase classified, for example, under EC 1.1.1.B3, EC 1.1.1.B4, or EC 1.1.1.80 (e.g., SEQ ID NO:4, SEQ ID NO: 9 or SEQ ID NO: 11). See FIG. 1.

Cultivation Strategy

In some embodiments 1,3-BDO is biosynthesized in a recombinant host using anaerobic, aerobic or micro-aerobic cultivation conditions. In some embodiments, the cultivation strategy entails nutrient limitation such as nitrogen, phosphate or oxygen limitation.

In some embodiments, a cell retention strategy using, for example, fiber membranes can be employed to achieve and maintain a high cell density during either fed-batch or continuous fermentation.

In some embodiments, the principal carbon source fed to the fermentation in the synthesis of 1,3-BDO can derive from biological or non-biological feedstocks.

In some embodiments, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as *Escherichia coli, Cupriavidus necator, Pseudomonas oleavorans, Pseudomonas putida* and *Yarrowia lipolytica* (Lee et al., *Appl. Biochem. Biotechnol.*, 2012, 166:1801-1813; Yang et al., *Biotechnology for Biofuels*, 2012, 5:13; Meijnen et al., *Appl. Microbiol. Biotechnol.*, 2011, 90:885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, 2011, supra; Martin and Prather, *J. Biotechnol.*, 2009, 139:61-67).

The efficient catabolism of lignin-derived aromatic compounds such as benzoate analogues has been demonstrated in several microorganisms such as *Pseudomonas putida, Cupriavidus necator* (Bugg et al., *Current Opinion in Biotechnology*, 2011, 22, 394-400; Pérez-Pantoja et al., *FEMS Microbiol. Rev.*, 2008, 32, 736-794).

The efficient utilization of agricultural waste, such as olive mill waste water has been demonstrated in several microorganisms, including *Yarrowia lipolytica* (Papanikolaou et al., *Bioresour. Technol.*, 2008, 99(7):2419-2428).

The efficient utilization of fermentable sugars such as monosaccharides and disaccharides derived from cellulosic, hemicellulosic, cane and beet molasses, cassava, corn and other agricultural sources has been demonstrated for several microorganism such as *Escherichia coli, Corynebacterium* glutamicum and *Lactobacillus delbrueckii* and *Lactococcus lactis* (see, e.g., Hermann et al, *J. Biotechnol.*, 2003, 104: 155-172; Wee et al., *Food Technol. Biotechnol.*, 2006, 44(2):163-172; Ohashi et al., *J. Bioscience and Bioengineering*, 1999, 87(5):647-654).

The efficient utilization of furfural, derived from a variety of agricultural lignocellulosic sources, has been demonstrated for *Cupriavidus necator* (Li et al., *Biodegradation*, 2011, 22:1215-1225).

In some embodiments, the non-biological feedstock can be or can derive from natural gas, syngas, $CO_2/H_2$, methanol, ethanol, benzoate, non-volatile residue (NVR) or a caustic wash waste stream from cyclohexane oxidation processes, or terephthalic acid/isophthalic acid mixture waste streams.

The efficient catabolism of methanol has been demonstrated for the methylotrophic yeast *Pichia pastoris*.

The efficient catabolism of ethanol has been demonstrated for *Clostridium kluyveri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society*, 2012, 2:11).

The efficient catabolism of syngas has been demonstrated for numerous microorganisms, such as *Clostridium ljungdahlii* and *Clostridium autoethanogenum* (Köpke et al., *Applied and Environmental Microbiology*, 2011, 77(15): 5467-5475).

The efficient catabolism of the non-volatile residue waste stream from cyclohexane processes has been demonstrated for numerous microorganisms, such as *Delftia acidovorans* and *Cupriavidus necator* (Ramsay et al., *Applied and Environmental Microbiology*, 1986, 52(1):152-156).

In some embodiments, the host microorganism is a prokaryote. For example, the prokaryote can be a bacterium from the genus *Escherichia* such as *Escherichia coli*; from the genus Clostridia such as *Clostridium ljungdahlii, Clostridium autoethanogenum* or *Clostridium kluyveri*; from the genus Corynebacteria such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*. Such prokaryotes also can be a source of genes to construct recombinant host cells described herein that are capable of producing 1,3-BDO.

In some embodiments, the host microorganism is a eukaryote. For example, the eukaryote can be a filamentous fungus, e.g., one from the genus *Aspergillus* such as *Aspergillus niger*. Alternatively, the eukaryote can be a yeast, e.g., one from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*. Such eukaryotes also can be a source of genes to construct recombinant host cells described herein that are capable of producing 1,3-BDO.

Metabolic Engineering

The present document provides methods involving less than all the steps described for all the above pathways. Such methods can involve, for example, one, two, three, four, five, six, seven, eight, nine, ten, eleven, twelve or more of such steps. Where less than all the steps are included in such a method, the first, and in some embodiments the only, step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host. This document provides host cells of any of the genera and species listed and genetically engineered to express one or more (e.g., two, three, four, five, six, seven, eight, nine, 10, 11, 12 or more) recombinant forms of any of the enzymes recited in the document. Thus, for example, the host cells can contain exogenous nucleic acids encoding enzymes catalyzing one or more of the steps of any of the pathways described herein.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined herein are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined here can be gene dosed, i.e., overexpressed, into the resulting genetically modified organism via episomal or chromosomal integration approaches.

In some embodiments, genome-scale system biology techniques such as Flux Balance Analysis can be utilized to devise genome scale attenuation or knockout strategies for directing carbon flux to 1,3-BDO.

Attenuation strategies include, but are not limited to; the use of transposons, homologous recombination (double cross-over approach), mutagenesis, enzyme inhibitors and RNAi interference.

In some embodiments, fluxomic, metabolomic and transcriptomal data can be utilized to inform or support genome-scale system biology techniques, thereby devising genome scale attenuation or knockout strategies in directing carbon flux to 1,3-BDO.

In some embodiments, the host microorganism's tolerance to high concentrations of 1,3-BDO can be improved through continuous cultivation in a selective environment.

In some embodiments, the host microorganism's endogenous biochemical network can be attenuated or augmented to (1) ensure the intracellular availability of acetyl-CoA and malonyl-CoA, (2) create an NADH or NADPH imbalance that may only be balanced via the formation of 1,3-BDO, (3) prevent degradation of central metabolites, central precursors leading to and including one or more 1,3-BDO and/or (4) ensure efficient efflux from the cell.

In some embodiments requiring intracellular availability of acetyl-CoA, endogenous enzymes catalyzing the hydrolysis of acetyl-CoA such as short-chain length thioesterases can be attenuated in the host organism.

In some embodiments requiring the intracellular availability of acetyl-CoA, an endogenous phosphotransacetylase generating acetate such as pta can be attenuated (Shen et al., *Appl. Environ. Microbiol.*, 2011, 77(9):2905-2915).

In some embodiments requiring the intracellular availability of acetyl-CoA, an endogenous gene in an acetate synthesis pathway encoding an acetate kinase, such as ack, can be attenuated.

In some embodiments requiring the intracellular availability of acetyl-CoA and NADH for 1,3-BDO synthesis, an endogenous gene encoding an enzyme that catalyzes the degradation of pyruvate to lactate such as lactate dehydrogenase encoded by ldhA can be attenuated (Shen et al., 2011, supra).

In some embodiments, enzymes that catalyze anapleurotic reactions such as PEP carboxylase and/or pyruvate carboxylase can be overexpressed in the host organism.

In some embodiments requiring the intracellular availability of acetyl-CoA and NADH for 1,3-BDO synthesis, endogenous genes encoding enzymes, such as menaquinol-fumarate oxidoreductase, that catalyze the degradation of phophoenolpyruvate to succinate such as frdBC can be attenuated (see, e.g., Shen et al., 2011, supra).

In some embodiments requiring the intracellular availability of acetyl-CoA and NADH for 1,3-BDO synthesis, an endogenous gene encoding an enzyme that catalyzes the degradation of acetyl-CoA to ethanol such as the alcohol dehydrogenase encoded by adhE can be attenuated (Shen et al., 2011, supra).

In some embodiments requiring the intracellular availability of malonyl-CoA, acetyl-CoA carboxylase can be overexpressed in the host organism.

In some embodiments requiring the intracellular availability of malonyl-CoA, malonyl-CoA ACP transacylase can be attenuated or repressed in the host organism.

In some embodiments requiring the intracellular availability of malonyl-CoA, the regulator of β-oxidation encoded by fadR can be overexpressed in the host organism (Zhang et al., 2012, *Metabolic Engineering*, 14, 653-660).

In some embodiments, where pathways require excess NADH co-factor for 1,3-BDO synthesis, a recombinant formate dehydrogenase gene can be overexpressed in the host organism (Shen et al., 2011, supra).

In some embodiments, where pathways require excess NADH co-factor for 1,3-BDO synthesis, a recombinant NADH-consuming transhydrogenase can be attenuated.

In some embodiments, an endogenous gene encoding an enzyme that catalyzes the degradation of pyruvate to ethanol such as pyruvate decarboxylase can be attenuated.

In some embodiments requiring the intracellular availability of acetyl-CoA for 1,3-BDO synthesis, a recombinant acetyl-CoA synthetase such as the gene product of acs can be overexpressed in the microorganism (Satoh et al., *J. Bioscience and Bioengineering*, 2003, 95(4):335-341).

In some embodiments, carbon flux can be directed into the pentose phosphate cycle to increase the supply of NADPH by attenuating an endogenous glucose-6-phosphate isomerase (EC 5.3.1.9).

In some embodiments, carbon flux can be redirected into the pentose phosphate cycle to increase the supply of NADPH by overexpression a 6-phosphogluconate dehydrogenase and/or a transketolase (Lee et al., 2003, *Biotechnology Progress*, 19(5), 1444-1449).

In some embodiments, where pathways require excess NADPH co-factor in the synthesis of 1,3-BDO, a gene such as UdhA encoding a puridine nucleotide transhydrogenase can be overexpressed in the host organisms (Brigham et al., *Advanced Biofuels and Bioproducts*, 2012, Chapter 39, 1065-1090).

In some embodiments, where pathways require excess NADPH co-factor in the synthesis of 1,3-BDO, a recombinant glyceraldehyde-3-phosphate-dehydrogenase gene such as GapN can be overexpressed in the host organisms (Brigham et al., 2012, supra).

In some embodiments, where pathways require excess NADPH co-factor in the synthesis of 1,3-BDO, a recombinant malic enzyme gene such as maeA or maeB can be overexpressed in the host organisms (Brigham et al., 2012, supra).

In some embodiments, where pathways require excess NADPH co-factor in the synthesis of 1,3-BDO, a recombinant glucose-6-phosphate dehydrogenase gene such as zwf can be overexpressed in the host organisms (Lim et al., *J. Bioscience and Bioengineering*, 2002, 93(6), 543-549).

In some embodiments, where pathways require excess NADPH co-factor in the synthesis of 1,3-BDO, a recombinant fructose 1,6 diphosphatase gene such as fbp can be overexpressed in the host organisms (Becker et al., *J. Biotechnol.*, 2007, 132:99-109).

In some embodiments, where pathways require excess NADPH co-factor in the synthesis of 1,3-BDO, endogenous triose phosphate isomerase (EC 5.3.1.1) can be attenuated.

In some embodiments, where pathways require excess NADPH co-factor in the synthesis of 1,3-BDO, a recombinant glucose dehydrogenase such as the gene product of gdh can be overexpressed in the host organism (Satoh et al., *J. Bioscience and Bioengineering*, 2003, 95(4):335-341).

In some embodiments, endogenous enzymes facilitating the conversion of NADPH to NADH can be attenuated, such as the NADH generation cycle that may be generated via inter-conversion of glutamate dehydrogenases classified under EC 1.4.1.2 (NADH-specific) and EC 1.4.1.4 (NADPH-specific).

In some embodiments, an endogenous glutamate dehydrogenase (EC 1.4.1.3) that utilizes both NADH and NADPH as co-factors can be attenuated.

In some embodiments, the β-ketothiolase condensing 3-hydroxypropionyl-CoA and acetyl-CoA to 3-oxo-5-hydroxypentanoyl-CoA is enzyme engineered to be selective for the condensation of 3-hydroxpropionyl-CoA and acetyl-CoA.

In some embodiments using hosts that naturally accumulate polyhydroxyalkanoates, the endogenous polymer synthase enzymes can be attenuated in the host strain.

In some embodiments, the efflux of 1,3-BDO across the cell membrane to the extracellular media can be enhanced or amplified by genetically engineering structural modifications to the cell membrane or increasing any associated transporter activity for 1,3-BDO.

Producing 1,3-BDO Using a Recombinant Host

Typically, 1,3-BDO can be produced by providing a host microorganism and culturing the provided microorganism with a culture medium containing a suitable carbon source as described above. In general, the culture media and/or culture conditions can be such that the microorganisms grow to an adequate density and produce 1,3-BDO efficiently. For large-scale production processes, any method can be used such as those described elsewhere (Manual of Industrial Microbiology and Biotechnology, $2^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of 1,3-BDO. Once produced, any method can be used to isolate 1,3-BDO. For example, 1,3-BDO can be recovered selectively from the fermentation broth via adsorption processes or by distillation to achieve the desired product purity.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of producing 3-oxo-5-hydroxypentanoyl-CoA in a recombinant host, said method comprising:

enzymatically producing 3-hydroxypropionyl-CoA from malonyl-CoA using a polypeptide having CoA transferase activity, wherein said polypeptide having a CoA transferase has at least 90% sequence identity to the amino acid sequence set forth in SEQ ID NO: 5, 6, 7, 12 or 13; and enzymatically converting 3-hydroxypropionyl-CoA to 3-oxo-5-hydroxypentanoyl-CoA using a polypeptide having ß-ketothiolase activity classified under EC.

2.3.1.-, wherein said polypeptide having ß-ketothiolase activity has at least 90% sequence identity to the amino acid sequence set forth in SEQ ID NOs: 1 or 2 and is capable of converting 3-hydroxypropionyl-CoA to 3-oxo-5-hydroxypentanoyl-CoA, wherein at least one of said polypeptides is encoded by an exogenous nucleic acid sequence.

2. The method of claim 1, wherein said polypeptide having β-ketothiolase activity is classified under EC 2.3.1.16. or EC 2.3.1.174.

* * * * *